(12) United States Patent
Definis et al.

(10) Patent No.: US 12,102,402 B2
(45) Date of Patent: Oct. 1, 2024

(54) SLIPPER CLUTCH FOR SURGICAL TOOL BAILOUT

(71) Applicant: Cilag GmbH International, Zug (CH)

(72) Inventors: Raffaele Definis, Loveland, OH (US); Benjamin L. Bertram, Crestview, KY (US); Christopher Denzinger, Cincinnati, OH (US); Heather E. Knox, Cincinnati, OH (US); Mark D. Overmyer, Cincinnati, OH (US); Neil Markwardt, Redwood City, CA (US)

(73) Assignee: Cilag GmbH International, Zug (CH)

( * ) Notice: Subject to any disclaimer, the term of this patent is extended or adjusted under 35 U.S.C. 154(b) by 658 days.

(21) Appl. No.: 17/173,655

(22) Filed: Feb. 11, 2021

(65) Prior Publication Data

US 2022/0249182 A1 Aug. 11, 2022

(51) Int. Cl.
| | |
|---|---|
| A61B 34/37 | (2016.01) |
| A61B 10/02 | (2006.01) |
| A61B 10/04 | (2006.01) |
| A61B 17/128 | (2006.01) |
| A61B 17/28 | (2006.01) |

(Continued)

(52) U.S. Cl.
CPC .......... *A61B 34/37* (2016.02); *A61B 10/0233* (2013.01); *A61B 10/04* (2013.01); *A61B 17/128* (2013.01); *A61B 17/28* (2013.01); *A61B 17/3201* (2013.01); *A61B 17/3211* (2013.01); *A61B 18/14* (2013.01); *A61B 34/76* (2016.02); *A61B 2010/045* (2013.01); *A61B 2017/00115* (2013.01); *A61B 2018/00595* (2013.01);

(Continued)

(58) Field of Classification Search
None
See application file for complete search history.

(56) References Cited

U.S. PATENT DOCUMENTS

| | | | |
|---|---|---|---|
| 2013/0270321 A1 | 10/2013 | Marczyk | |
| 2016/0157941 A1* | 6/2016 | Anvari | A61B 34/70 279/143 |

(Continued)

OTHER PUBLICATIONS

Written Opinion and International Search Report from PCT corresponding PCT Application No. PCT/IB2022/051107 mailed May 13, 2022.

*Primary Examiner* — Yingchuan Zhang
*Assistant Examiner* — Jessica L Mullins
(74) *Attorney, Agent, or Firm* — Vorys, Sater, Seymour and Pease LLP

(57) ABSTRACT

A robotic surgical tool includes a handle having a drive input and a spline, a bailout ring arranged at the handle, and a slipper clutch mechanism received within the bailout ring. The slipper clutch mechanism including a slip carrier rotationally fixed to the bailout ring and defining a vertical slot that slidably receives a pin, a first ring arranged within the slip carrier and defining a first interface, a second ring arranged within the slip carrier atop the first ring and defining a second interface, and a pinion gear operatively coupled to the spline and arranged to intermesh with radial gear teeth defined on the second ring. Manual rotation of the bailout ring rotates the slip carrier and the pin and thereby rotates the first and second ring in succession to rotate the spline and manually bail out a function of the robotic surgical tool.

16 Claims, 28 Drawing Sheets

(51) Int. Cl.
*A61B 17/3201* (2006.01)
*A61B 17/3211* (2006.01)
*A61B 18/14* (2006.01)
*A61B 34/00* (2016.01)
*A61B 17/00* (2006.01)
*A61B 18/00* (2006.01)
*A61B 34/30* (2016.01)

(52) U.S. Cl.
CPC ......... *A61B 34/30* (2016.02); *A61B 2034/305* (2016.02); *Y10T 70/70* (2015.04)

(56) References Cited

U.S. PATENT DOCUMENTS

2018/0049836 A1\* 2/2018 Shelton, IV ..... A61B 17/00234
2018/0051780 A1  2/2018 Shelton, IV et al.
2019/0038281 A1  2/2019 Shelton, IV et al.

\* cited by examiner

SLIPPER CLUTCH FOR SURGICAL TOOL BAILOUT

TECHNICAL FIELD

The systems and methods disclosed herein are directed to robotic surgical tools and, more particularly to, tool bailout systems that employ one or more manually actuatable bailout rings.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms manipulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a handle having a drive input and a spline operatively coupled to the drive input, wherein rotating the spline causes operation of a function of the robotic surgical tool, a bailout ring arranged at the handle, a slipper clutch mechanism received within the bailout ring and including a slip carrier rotationally fixed to the bailout ring and defining a vertical slot that slidably receives a pin, a first ring arranged within the slip carrier and defining a first interface, a second ring arranged within the slip carrier atop the first ring and defining a second interface, and a pinion gear operatively coupled to the spline and arranged to intermesh with radial gear teeth defined on the second ring, wherein manual rotation of the bailout ring rotates the slip carrier and the pin in the same direction and thereby rotates the first ring when the pin is received within the first interface, wherein manual rotation of the bailout ring rotates the second ring once the pin locates and is received within the second interface, and wherein rotating the second ring drives the pinion gear and rotates the spline to manually bail out the function of the robotic surgical tool. In a further embodiment, the robotic surgical tool further includes a drive housing that includes the handle at a first end and has a lead screw extending from the handle, a carriage movably mounted to the lead screw such that rotation of the lead screw from the handle causes the carriage to move axially along the lead screw, and an elongate shaft extending from the carriage and penetrating the handle, the shaft having an end effector arranged at a distal end thereof, wherein the function of the robotic surgical tool is selected from the group consisting of translating a knife at the end effector, opening or closing opposing jaws of the end effector, articulating an orientation of the end effector at a wrist interposing the shaft and the end effector, retracting a biopsy needle, disconnecting electrocautery, opening scissors, releasing a clip, translation of the handle, decoupling, and locking of an insertion drive. In another further embodiment, the drive input is a first drive input, the spline is a first spline, the function is a first function, and the pinion gear is a first pinion gear, the robotic surgical tool further comprising a second drive input arranged at the handle and a second spline operatively coupled to the second drive input and rotatable to cause operation of a second function of the robotic surgical tool, and wherein the slipper clutch mechanism further includes a crown gear arranged atop the second ring, a bailout device including a knob and a drive gear engageable with gear teeth defined on the crown gear, and a second pinion gear operatively coupled to the second spline and arranged to intermesh with radial gear teeth defined on the crown gear, wherein manual rotation of the knob rotates the crown gear and thereby rotates the second spline to manually bail out the second function of the robotic surgical tool. In another further embodiment, the robotic surgical tool further includes one or more markings provided on a housing of the handle and indicating a corresponding one or more conditions of the function of the robotic surgical tool, wherein rotating the knob to align with the a given marking of the one or more markings will transition the function of the robotic surgical tool to a condition of one or more conditions corresponding to the given marking. In another further embodiment, the slipper clutch mechanism further includes a third ring interposing the first and second rings and defining a third interface, the third ring being rotatable relative to the first and third rings, and wherein manual rotation of the bailout ring rotates the third ring once the pin locates and is received within the third interface. In another further embodiment, the spline is operatively coupled to the drive input via a drive shaft extending from the drive input, and wherein the slipper clutch mechanism further includes a decoupling mechanism that comprises a ramp defined on an inner surface of the first ring, and a decoupling plunger cap mounted to the drive shaft and providing a radial flange engageable with the ramp, wherein rotating the first ring moves the ramp into engagement with the radial flange and thereby moves the decoupling plunger cap relative to drive shaft to decouple the drive input from a drive output of an instrument driver. In another further embodiment, the slipper clutch mechanism further includes an anti-reverse mechanism that includes a spring-actuated pawl engageable with ratchet teeth defined on an inner surface of the slip carrier, wherein the pawl allows the slip carrier to rotate in a first direction, but engages the ratchet teeth to prevent the slip carrier from rotating in a second direction opposite the first direction. In another further embodiment, operation of the anti-reverse mechanism provides audible or tactile feedback to a user. In another further embodiment, the slipper clutch mechanism further includes a latch lock defeat mechanism that includes a column, a lifter having a foot received within a pocket defined in the column, a lifter shaft extending from the foot, and a locking tab arranged in the pocket that prevents the foot from exiting the pocket, and a ramp defined on the first ring and engageable with a lateral tab provided on the lifter shaft, wherein rotating the first ring moves the ramp into engagement with the lateral tab and moves the lifter proximally to transition the locking tab from a latched position, where the locking tab extends out of the pocket and inhibits unlatching of the handle from an instrument driver, and a released position, where the locking tab is stowed within the pocket and allows a latch ring to move and detach the handle from the instrument driver.

Embodiments disclosed herein further include a method of operating a robotic surgical tool, the method including arranging the robotic surgical tool adjacent a patient, the robotic surgical tool including a handle having a first drive input and a first spline operatively coupled to the first drive input and rotatable to operate a first function of the robotic surgical tool, a bailout ring arranged at the handle, and a slipper clutch mechanism received within the bailout ring, the slipper clutch mechanism including a slip carrier rotationally fixed to the bailout ring and defining a vertical slot that slidably receives a pin, a first ring arranged within the slip carrier and defining a first interface, a second ring arranged within the slip carrier atop the first ring and defining a second interface, and a first pinion gear operatively coupled to the spline and arranged to intermesh with radial gear teeth defined on the second ring. The method further including manually rotating the bailout ring and thereby rotating the slip carrier and the pin in the same direction, rotating the first ring with the pin received within the first interface, locating and entering the second interface with the pin as the first ring rotates, rotating the second ring with the pin received within the second interface, and driving the first pinion gear and the second spline with the second ring and thereby manually bailing out the first function of the robotic surgical tool. In a further embodiment, the robotic surgical tool further includes a drive housing that includes the handle at a first end and has a lead screw extending from the handle, a carriage movably mounted to the lead screw such that rotation of the lead screw from the handle causes the carriage to move axially along the lead screw, and an elongate shaft extending from the carriage and penetrating the handle, the shaft having an end effector arranged at a distal end thereof, and wherein the function of the robotic surgical tool is selected from the group consisting of translating a knife at the end effector; opening or closing opposing jaws of the end effector, and articulating an orientation of the end effector at a wrist interposing the shaft and the end effector, retracting a biopsy needle, disconnecting electrocautery, opening scissors, releasing a clip, translation of the handle, decoupling, and locking of an insertion drive. In another further embodiment, the robotic surgical tool further includes a second drive input arranged at the handle and a second spline operatively coupled to the second drive input and rotatable operate a second function of the robotic surgical tool, the slipper clutch mechanism further including a crown gear arranged atop the second ring, a bailout device including a knob and a drive gear engageable with gear teeth defined on the crown gear, and a second pinion gear operatively coupled to the second spline and arranged to intermesh with radial gear teeth defined on the crown gear, the method further including manually rotating the knob and thereby rotating the crown gear, and driving the second pinion gear and the second spline with the crown gear and thereby manually bailing out the second function of the robotic surgical tool. In another further embodiment, the slipper clutch mechanism further includes a third ring interposing the first and second rings and defining a third interface, the method further comprising locating and entering the third interface with the pin, and rotating the third ring with the pin received within the third interface. In another further embodiment, the spline is operatively coupled to the drive input via a drive shaft extending from the drive input, and wherein the slipper clutch mechanism further includes a decoupling mechanism that comprises a ramp defined on an inner surface of the first ring, and a decoupling plunger cap mounted to the drive shaft and providing a radial flange engageable with the ramp, wherein rotating the first ring comprises moving the ramp into engagement with the radial flange, moving the decoupling plunger cap relative to drive shaft with the ramp, and decoupling the drive input from a drive output of an instrument driver as the decoupling plunger cap moves. In another further embodiment, the slipper clutch mechanism further includes an anti-reverse mechanism that includes a spring-actuated pawl engageable with ratchet teeth defined on an inner surface of the slip carrier, the method further comprising allowing the slip carrier to rotate in a first direction with the pawl, and engaging the pawl on the ratchet teeth and thereby preventing the slip carrier from rotating in a second direction opposite the first direction. In another further embodiment, the slipper clutch mechanism further includes a latch lock defeat mechanism that includes a column, a lifter having a foot received within a pocket defined in the column, a lifter shaft extending from the foot, and a locking tab arranged in the pocket that prevents the foot from exiting the pocket, and a ramp defined on the first ring and engageable with a lateral tab provided on the lifter shaft, and wherein rotating the first ring comprises moving the ramp into engagement with the lateral tab, and moving the lifter proximally via engagement with the ramp and thereby transitioning the locking tab from a latched position, where the locking tab extends out of the pocket and inhibits unlatching of the handle from an instrument driver, and a released position, where the locking tab is stowed within the pocket and allows a latch ring to move and detach the handle from the instrument driver.

Embodiments disclosed herein further include a slipper clutch bailout mechanism for a robotic surgical tool that includes a ring gear defining ratchet teeth and being operatively coupled to a spline via a drive mechanism such that rotation of the ring gear correspondingly rotates the spline and causes operation of a function of the robotic surgical tool, and a manually rotatable bailout ring axially offset from the ring gear and providing one or more engagement features engageable with the ratchet teeth, wherein manual rotation of the bailout ring in a first direction with the one or more engagement features engaged with the ratchet teeth rotates the spline to manually bail out the function of the robotic surgical tool. In a further embodiment, the drive mechanism comprises a gear train including a plurality of intermeshed gears extending between inner radial teeth defined on an inner radial surface of the ring gear and a pinion gear coupled to the spline. In another further embodiment, manual rotation of the bailout ring in a second direction opposite the first direction causes the one or more engagement features to ratchet over the ratchet teeth. In another further embodiment, the slipper clutch bailout mechanism further includes one or more springs arranged to provide a downward force on the bailout ring and thereby promote engagement of the one or more engagement features with the ratchet teeth.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
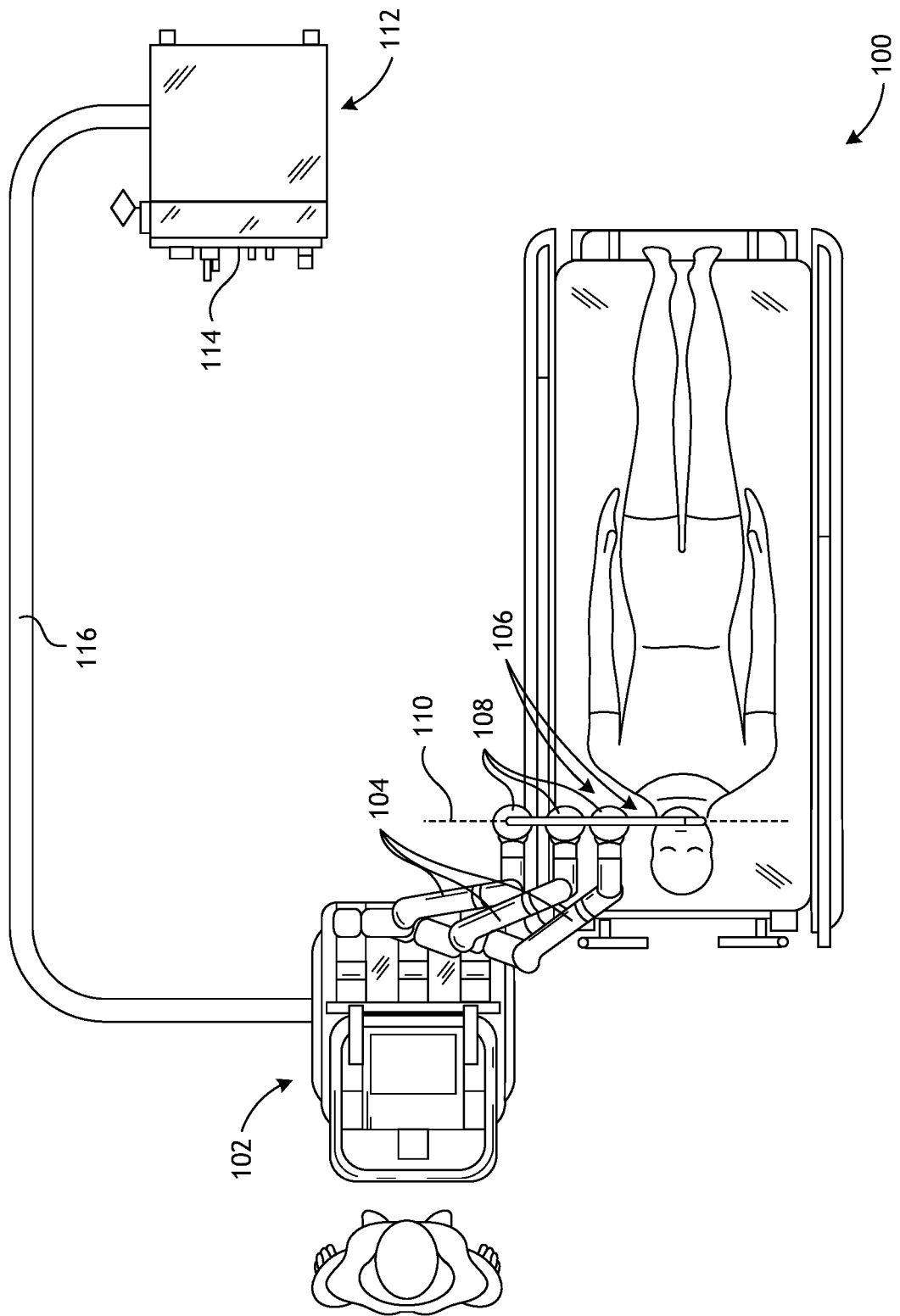
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108 (alternately referred to as "tool drivers"). As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching the target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of the target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof.

For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for the sensors deployed throughout the robotic system 100. For example, the tower 112 may include opto-electronics equipment for detecting, receiving, and processing data received from the optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
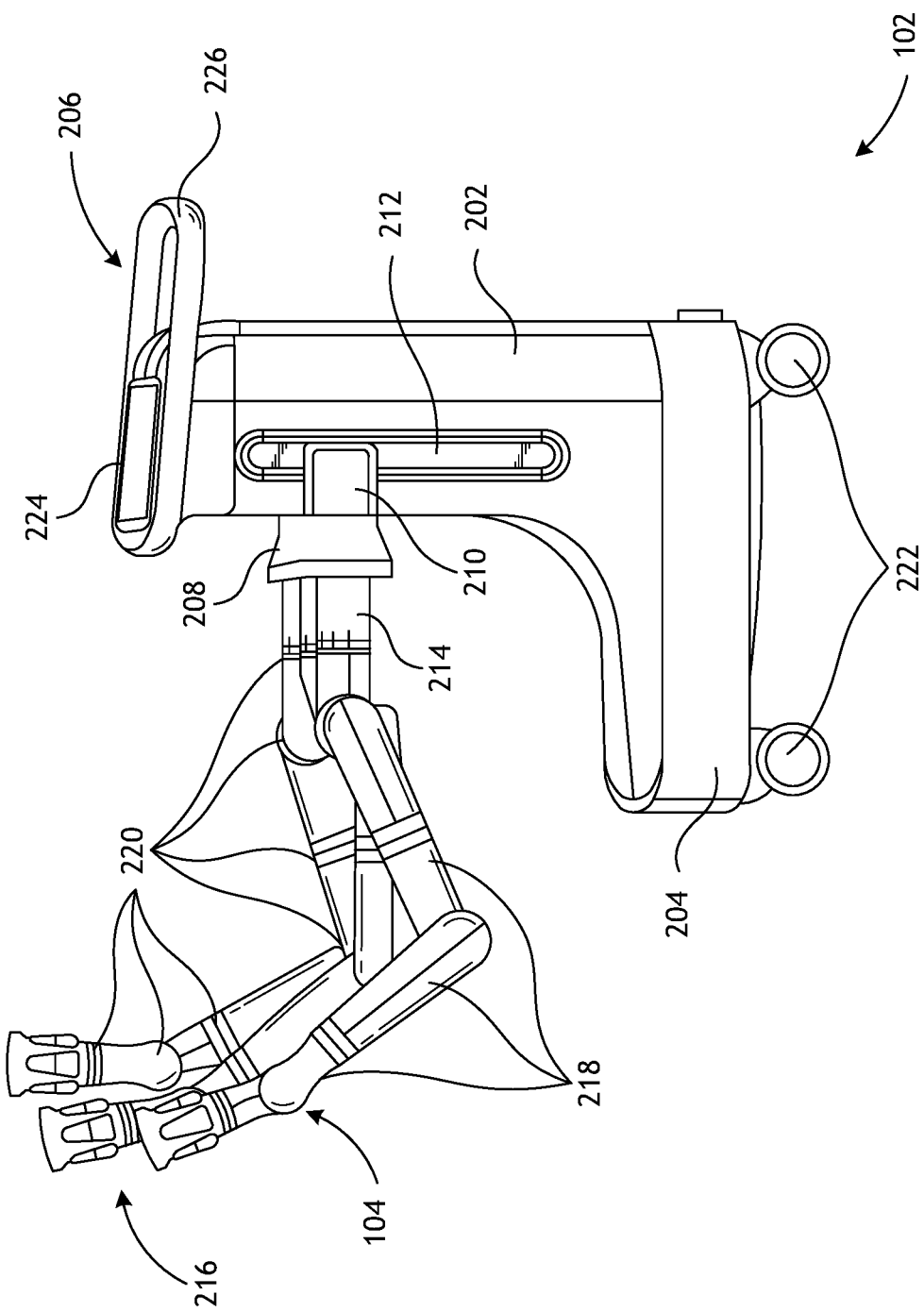
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (often referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage 218 positions and joint 220 angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rollable wheel-shaped casters 222 that allow for the cart to easily move around the room prior to a procedure. After reaching the appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
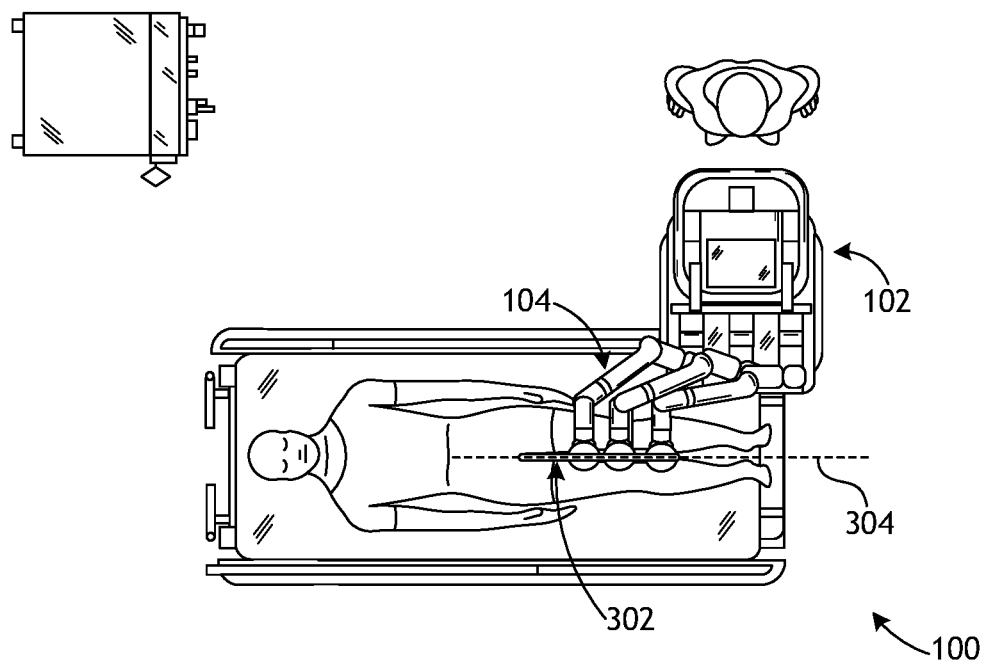
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy in the area. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 302 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down the working channel of the ureteroscope 302. After lithotripsy is complete, the resulting stone fragments may be removed using baskets deployed down the ureteroscope 302.

Figure 3B:
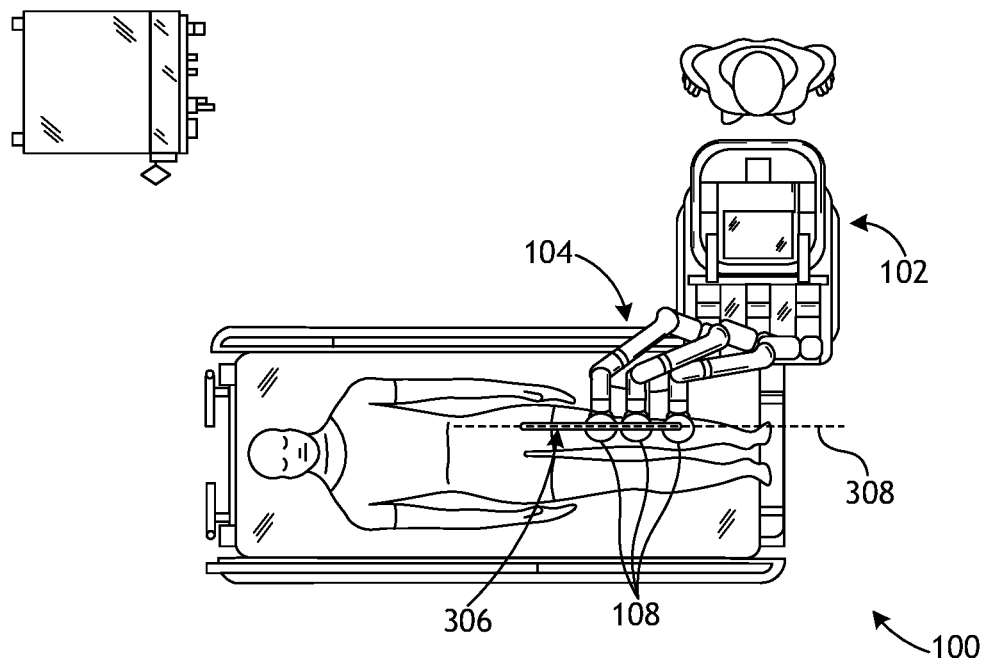
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and inserted by translating the instrument drivers 108. Alternatively, the cart 102 may be positioned around the patient's upper abdomen in order to reach alternative vascular access points, such as, for example, the carotid and brachial arteries near the shoulder and wrist.

B. Robotic System—Table

Figure 4:
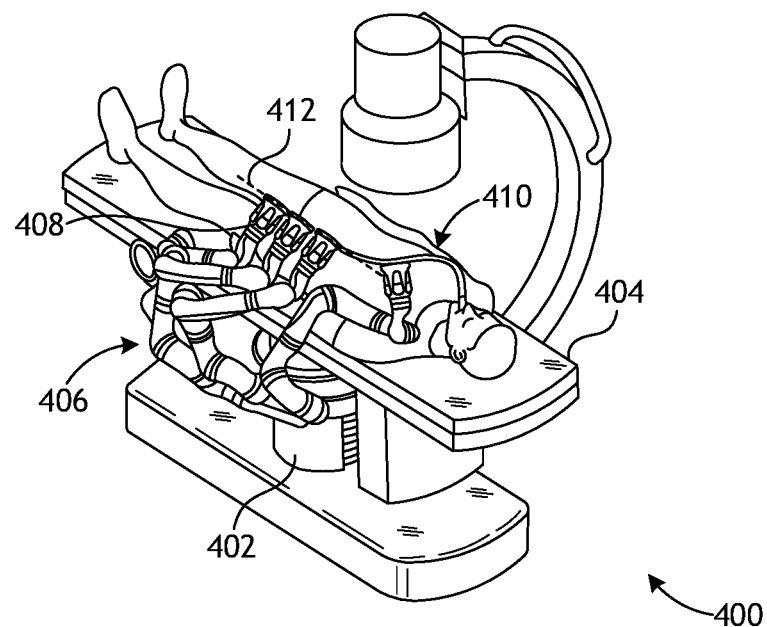
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 (alternately referred to as "tool drivers") that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
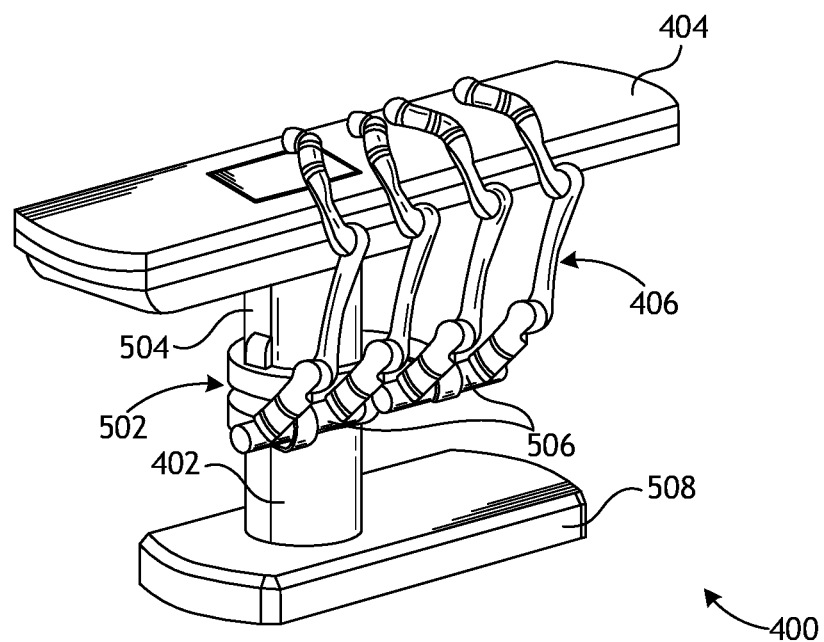
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align the medical instruments, such as endoscopes and laparoscopes, into different access points on the patient.

In other embodiments (not shown), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
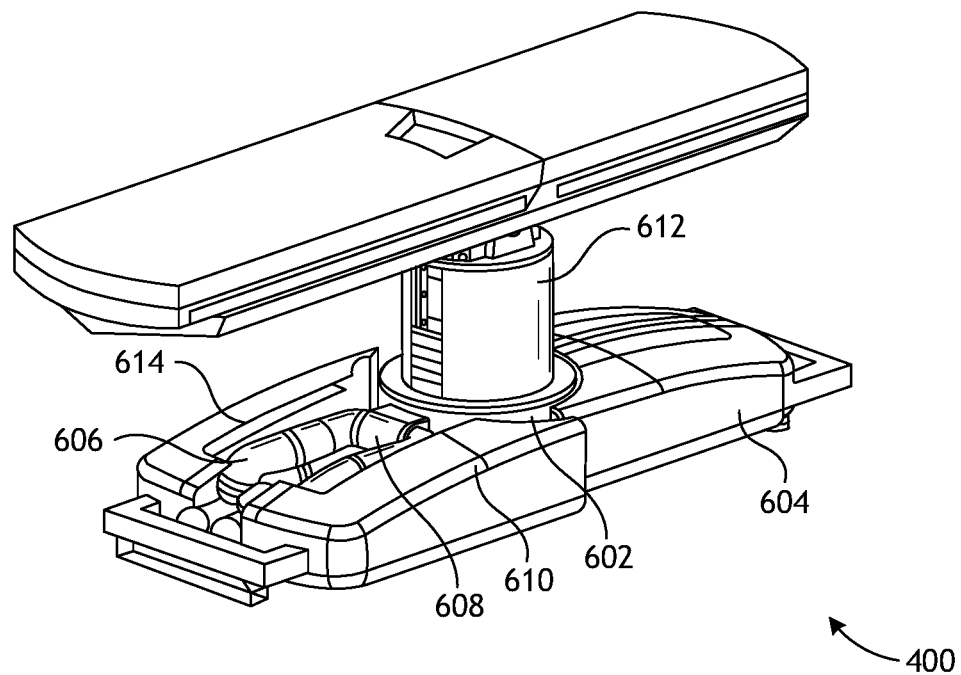
FIG. 6 illustrates an example system configured to stow robotic arm(s).

In some embodiments, a table base may stow and store the robotic arms when not in use. FIG. 6 illustrates an embodiment of the system 400 that stows robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
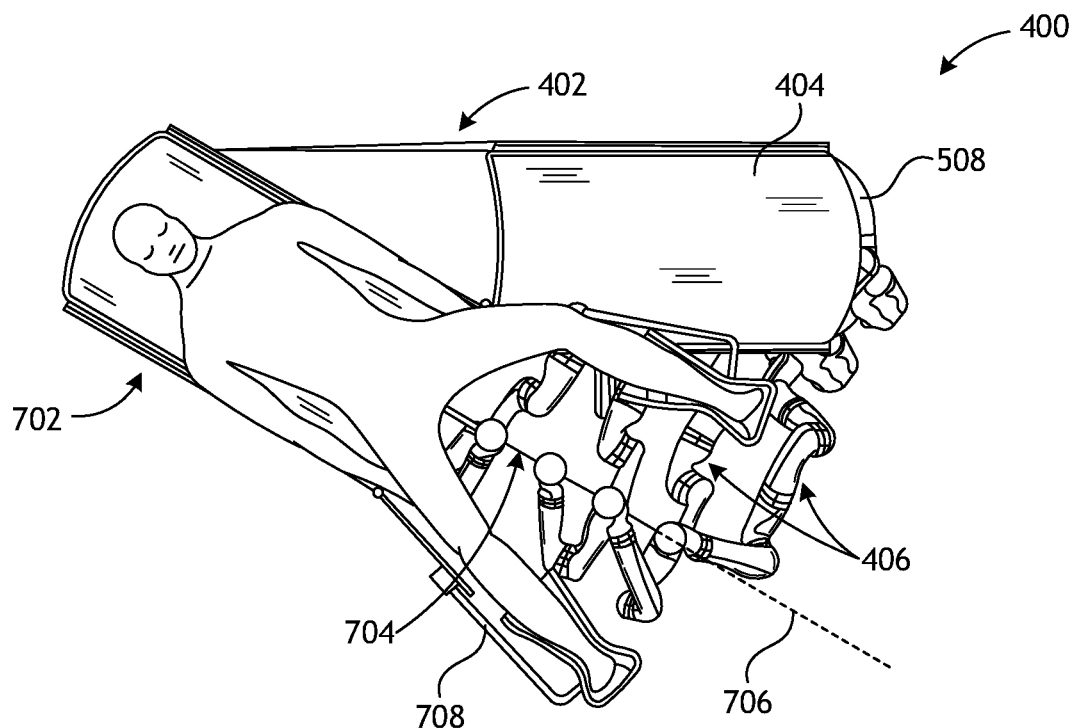
FIG. 7A illustrates an embodiment of a table-based robotic system configured for a ureteroscopy procedure.
Figure 7B:
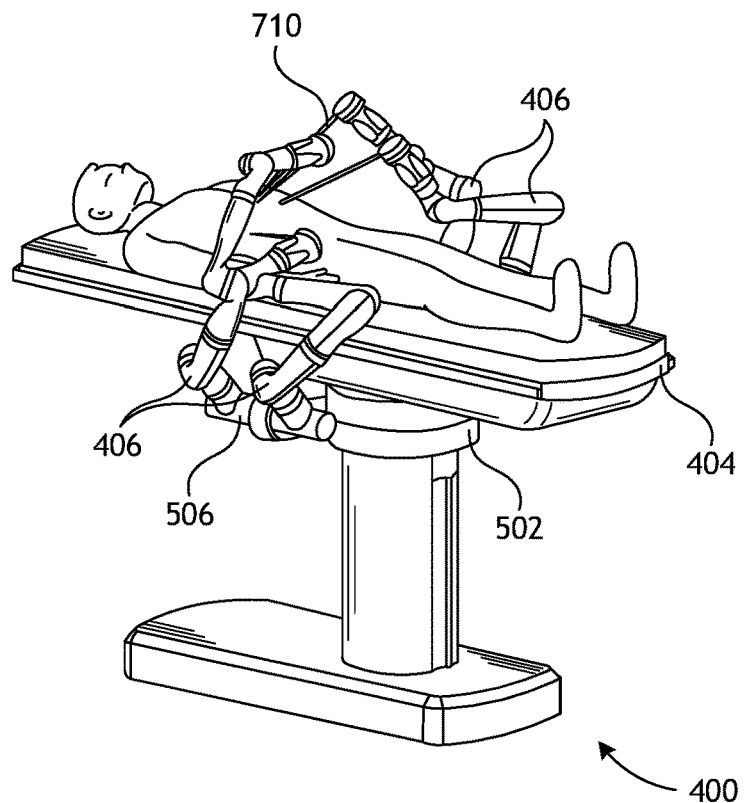
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
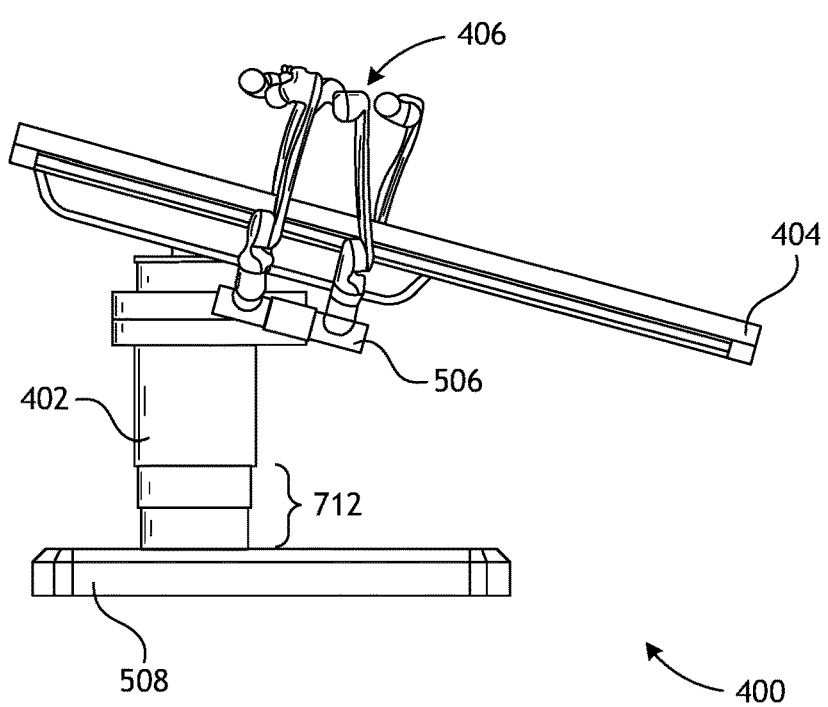
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
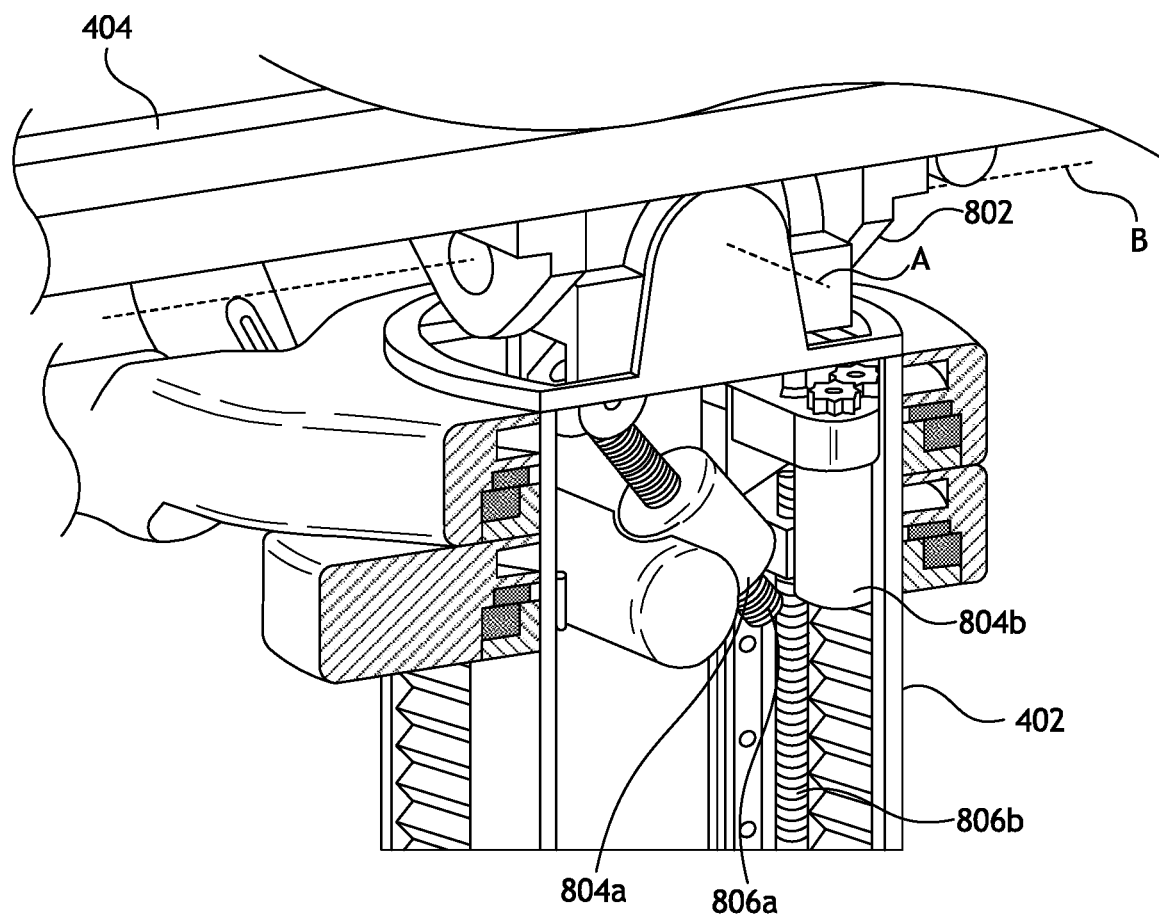
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
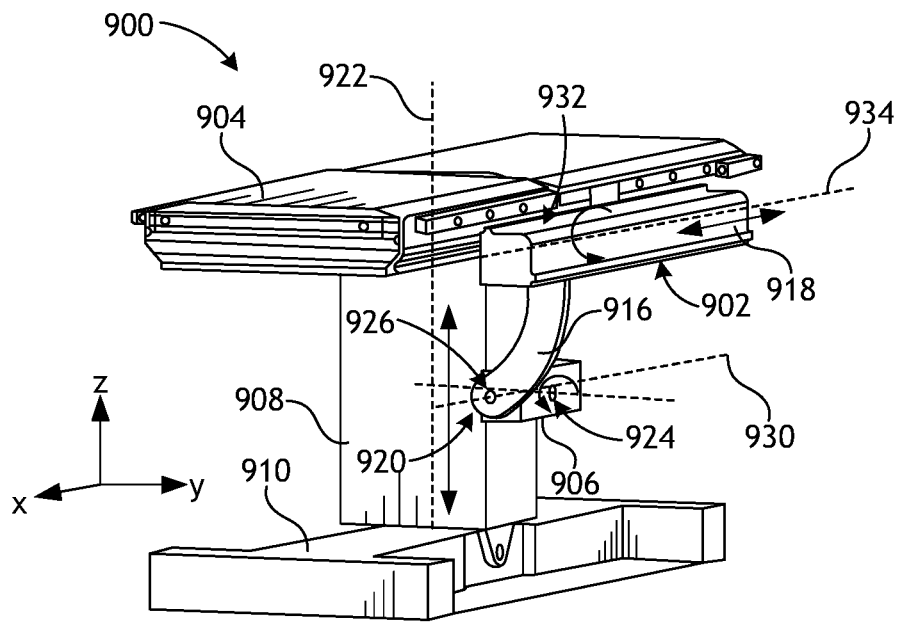
FIG. 9A illustrates an alternative embodiment of a table-based robotic system.
Figure 9B:
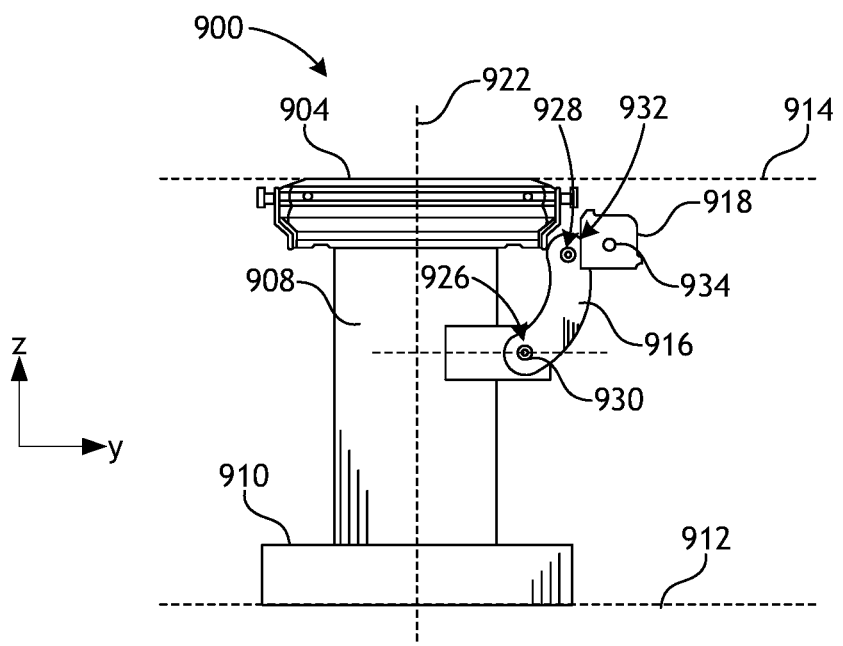
FIG. 9B illustrates an end view of the table-based robotic system of FIG. 9A.

FIGS. 9A and 9B illustrate isometric and end views, respectively, of an alternative embodiment of a table-based surgical robotics system 15000. The surgical robotics system 15000 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 15000, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 15000 in FIGS. 9A and 9B can comprise a table supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
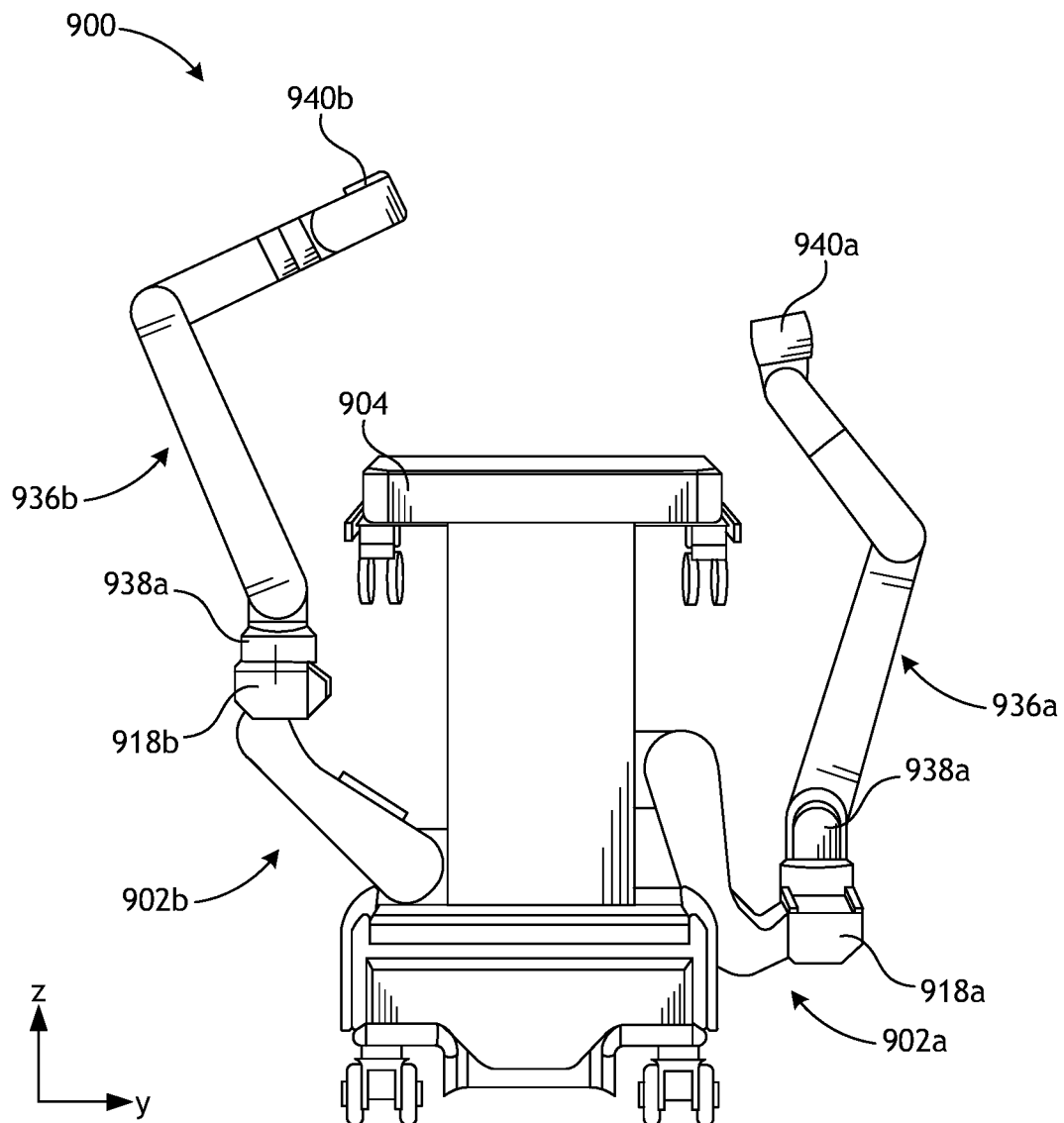
FIG. 9C illustrates an end view of a table-based robotic system with robotic arms attached thereto.

FIG. 9C illustrates an end view of the surgical robotics system 15000 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface

The end effectors of the system's robotic arms comprise (i) an instrument driver (alternatively referred to as "tool driver," "instrument drive mechanism," "instrument device manipulator," and "drive input") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
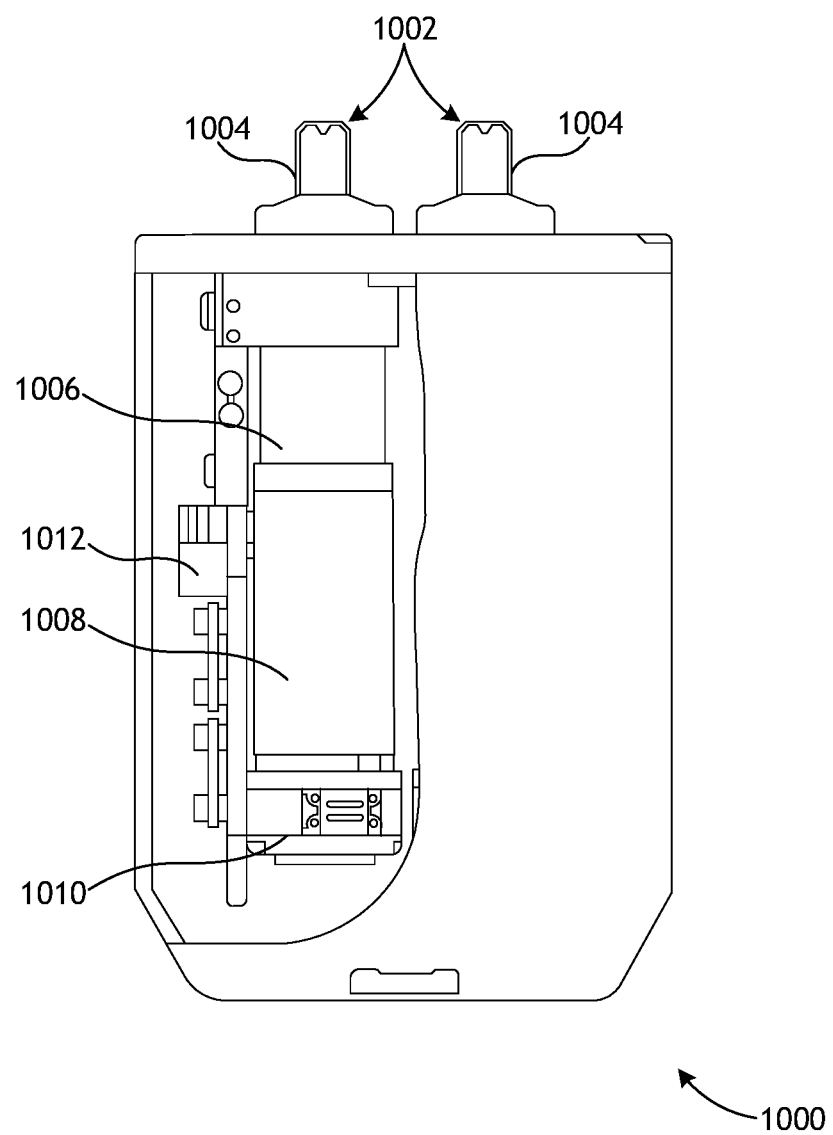
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive units 1002 arranged with parallel axes to provide controlled torque to a medical instrument via corresponding drive shafts 1004. Each drive unit 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive unit 1002. Each drive unit 1002 being independent controlled and motorized, the instrument driver 1000 may provide multiple (at least two shown in FIG. 10) independent drive outputs to the medical instrument. In operation, the control circuitry 1012 would receive a control signal, transmit a motor signal to the motor 1008, compare the resulting motor speed as measured by the encoder 1010 with the desired speed, and modulate the motor signal to generate the desired torque.

For procedures that require a sterile environment, the robotic system may incorporate a drive interface, such as a sterile adapter connected to a sterile drape, which sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 11:
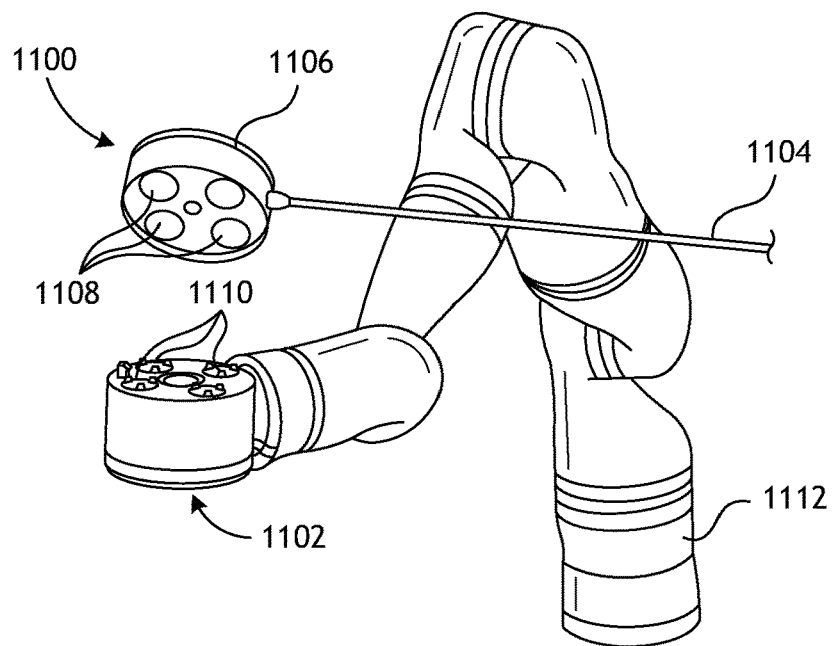
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 72. From the handle 72, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
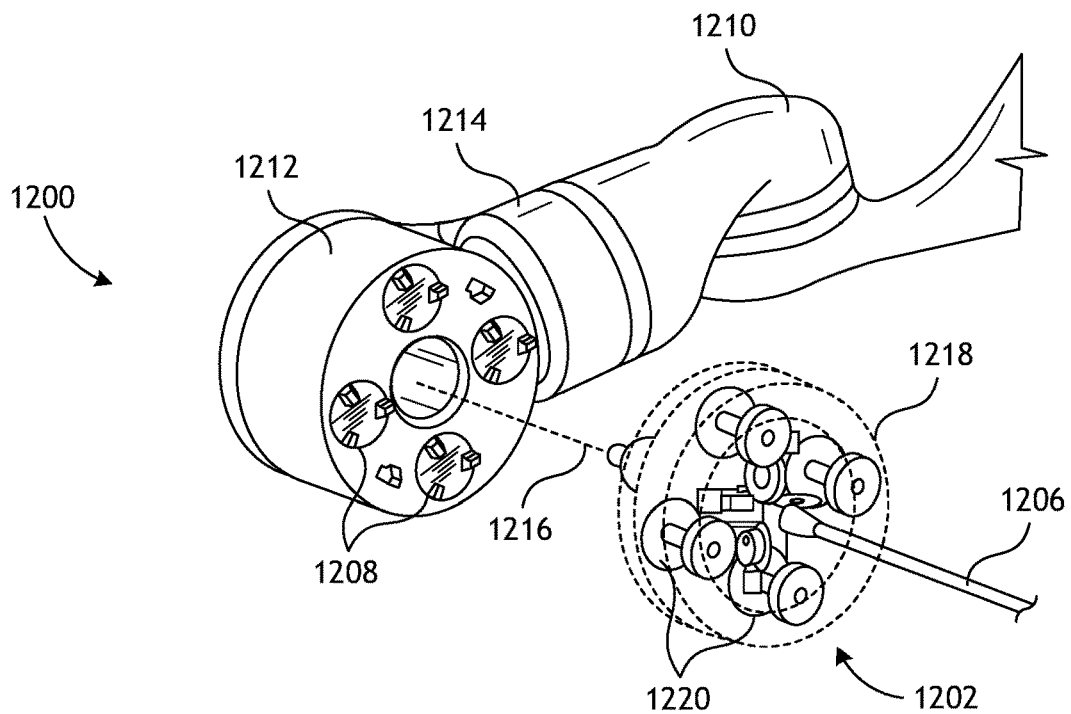
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and controls signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mat with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
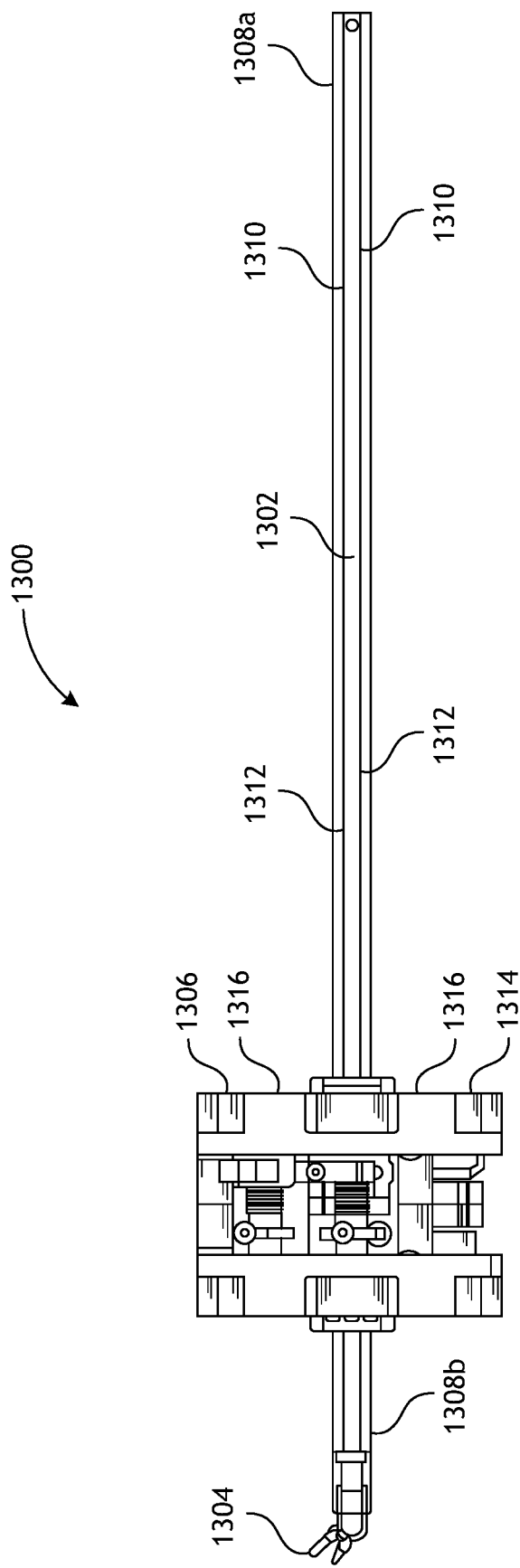
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more torque couplers on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
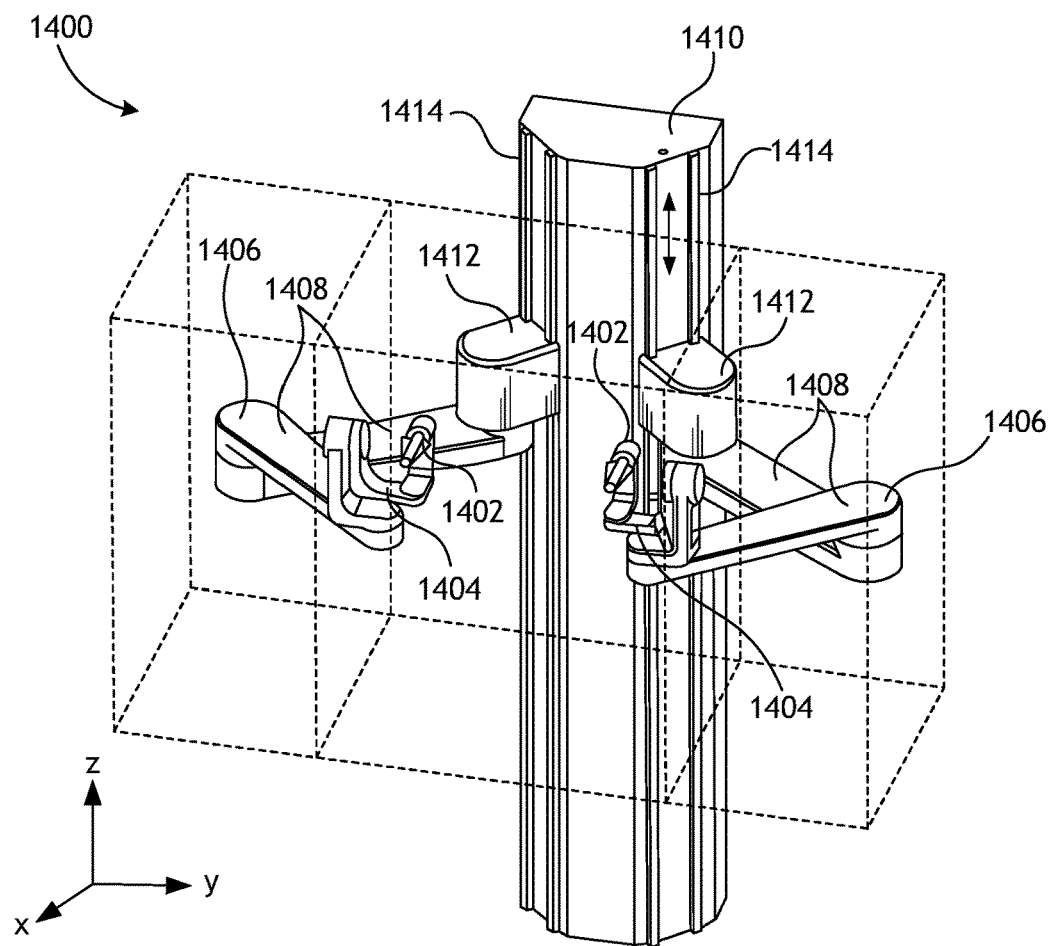
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
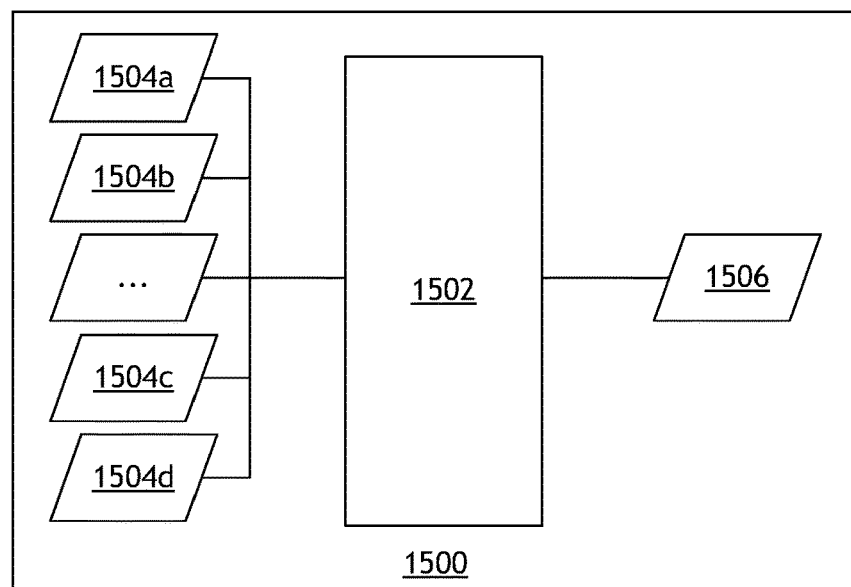
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504*a*, 1504*b*, 1504*c*, and 1504*d* to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504*a-d* are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504*a* (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504*b*. The localization module 1502 may process the vision data 1504*b* to enable one or more vision-based location tracking. For example, the preoperative model data may be used in conjunction with the vision data 1504*b* to enable computer vision-based tracking of the medical instrument (e.g., an endoscope or an instrument advance through a working channel of the endoscope). For example, using the preoperative model data 1504*a*, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504$a$-$d$ in combination(s). In some cases, such a combination may use a probabilistic approach where the localization module 1502 assigns a confidence weight to the location determined from each of the input data 1504$a$-$d$. Thus, where the EM data 1504$c$ may not be reliable (as may be the case where there is EM interference) the confidence of the location determined by the EM data 1504$c$ can be decrease and the localization module 1502 may rely more heavily on the vision data 1504$b$ and/or the robotic command and kinematics data 1504$d$.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Implementing Systems and Discussion

Embodiments of the disclosure relate to systems and techniques of manually bailing out a robotic surgical tool. The robotic surgical tool includes a handle having a drive input and a spline operatively coupled to the drive input, wherein rotating the spline causes operation of a function of the robotic surgical tool. A bailout ring may be arranged at the handle, and a slipper clutch mechanism is received within the bailout ring. The slipper clutch mechanism may include a slip carrier rotationally fixed to the bailout ring and defining a vertical slot that slidably receives a pin, a first ring arranged within the slip carrier and defining a first interface, a second ring arranged within the slip carrier atop the first ring and defining a second interface, and a pinion gear operatively coupled to the spline and arranged to intermesh with radial gear teeth defined on the second ring. Manual rotation of the bailout ring may rotate the slip carrier and the pin in the same direction and thereby rotate the first ring when the pin is received within the first interface. Manual rotation of the bailout ring may further rotate the second ring once the pin locates and is received within the second interface, and rotating the second ring may drive the pinion gear and rotate the spline to manually bail out the function of the robotic surgical tool.

Figure 16:
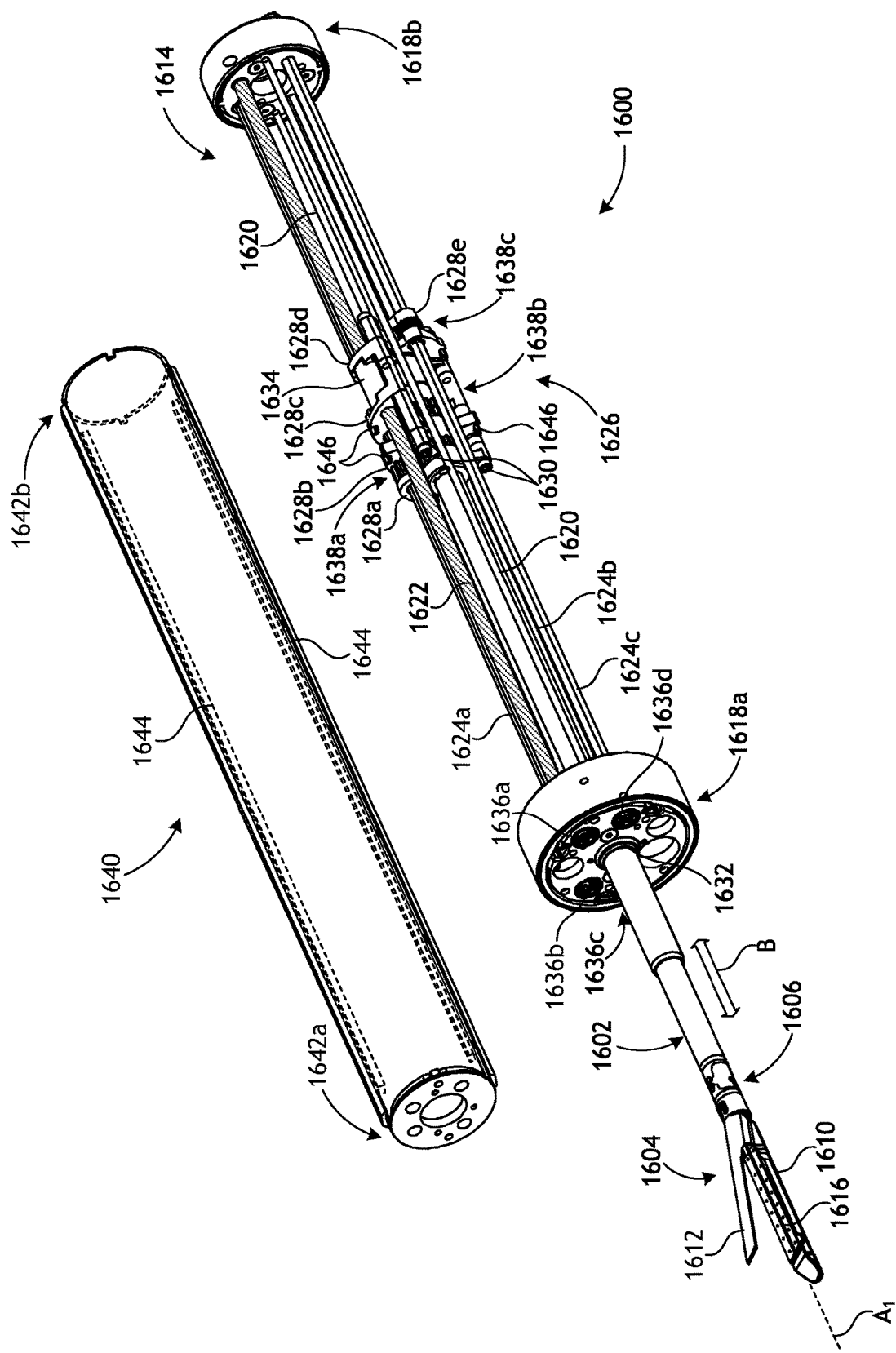
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments having opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, however, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions; i.e., bifurcating jaws.

In the illustrated example, the first jaw 1610 is referred to as a "cartridge" or "channel" jaw, and the second jaw 1612 is referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing 1614 that houses or includes an actuation system designed to facilitate articulation of the wrist 1606 and actuation (operation) of the end effector 1604 (e.g., clamping, firing, rotation, opening/closing, energy delivery, etc.). As described in more detail below, the drive housing 1614, alternately referred to as a "stage," provides various coupling features that releasably couple the surgical tool 1600 to an instrument driver of a robotic surgical system.

The drive housing 1614 includes a plurality of drive members (obscured in FIG. 16), such as cables, bands, lines, cords, wires, ropes, strings, twisted strings, or elongate members, which extend to the wrist 1606 and the end effector 1604. Selective actuation of one or more of the drive members can cause the end effector 1604 to articulate (pivot) relative to the shaft 1602 at the wrist 1606. Selective actuation of one or more other drive members can cause the end effector 1604 to actuate (operate). Actuating the end effector 1604 may include closing and/or opening the jaws, 1610, 1612, and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot 1616 defined in the first jaw 1610. As it moves distally, the knife transects any tissue grasped between the opposing jaws 1610, 1612. Moreover, as the knife advances distally, a plurality of staples contained within the staple cartridge (e.g., housed within the first jaw 1610) are urged (cammed) into deforming contact with corresponding anvil surfaces (e.g., pockets) provided on the opposing second jaw 1612. The deployed staples may form multiple rows of staples that seal opposing sides of the transected tissue.

As illustrated, the drive housing 1614 has a first or "distal" end 1618*a* and a second or "proximal" end 1618*b* opposite the first end 1618*a*. The first end 1618*a* is alternately referred to as a "handle" because it is typically gripped by a user when attaching the surgical tool 1600 to an instrument driver. In some embodiments, one or more struts 1620 (two shown) extend longitudinally between the first and second ends 1618*a,b* to help fix the distance between the first and second ends 1618*a,b*, provide structural stability to the drive housing 1614, and secure the first end 1618*a* to the second end 1618*b*. In other embodiments, however, the struts 1620 may be omitted, without departing from the scope of the disclosure.

The drive housing 1614 may also include a lead screw 1622 and one or more splines 1624, which also extend longitudinally between the first and second ends 1618*a,b*. In the illustrated embodiment, the drive housing 1614 includes a first spline 1624*a*, a second spline 1624*b*, and a third spline 1624*c*. While three splines 1624*a-c* are depicted in the drive housing 1614, more or less than three may be included in the surgical tool 1600. Unlike the struts 1620, the lead screw 1622 and the splines 1624*a-c* are rotatably mounted to the first and second ends 1618*a,b*. As discussed herein, selective rotation (actuation) of the lead screw 1622 and the splines 1624*a-c* causes various functions of the drive housing 1614 to transpire, such as translating the end effector 1604 along the longitudinal axis $A_1$ (e.g., z-axis translation), causing the end effector 1604 to articulate (pivot) at the wrist 1606, causing the jaws 1610, 1612 to open or close, and causing the end effector 1604 to fire (operate).

The drive housing 1614 further includes a carriage 1626 movably mounted along the lead screw 1622 and the splines 1624*a-c*, and housing various activating mechanisms configured to cause operation of specific functions of the end effector 1604. The carriage 1626 may comprise two or more layers, shown in FIG. 16 as a first layer 1628*a*, a second layer 1628*b*, a third layer 1628*c*, a fourth layer 1628*d*, and a fifth layer 1628*e*. The lead screw 1622 and the splines 1624*a-c* each extend through portions of one or more of the layers 1628*a-e* to allow the carriage 1626 to translate along the longitudinal axis $A_1$ with respect to (relative to) the lead screw 1622 and the splines 1624*a-c*. In some embodiments, the layers 1628*a-e* may be secured to each other in series using one or more mechanical fasteners 1630 (two visible) extending between the first layer 1628*a* and the fifth layer 1628*e* and through coaxially aligned holes defined in some or all of the layers 1628*a-e*. While five layers 1628*a-e* are depicted, the carriage 1626 can include more or less than five, without departing from the scope of the disclosure.

The shaft 1602 is coupled to and extends distally from the carriage 1626 through the first end 1618*a* of the drive housing 1614. In the illustrated embodiment, for example, the shaft 1602 penetrates the first end 1618*a* or "handle" at a central aperture 1632 defined through the first end 1618*a*. The carriage 1626 is movable between the first and second ends 1618*a,b* along the longitudinal axis $A_1$ (e.g., z-axis translation) and is thereby able to advance or retract the end effector 1604 relative to the drive housing 1614, as indicated by the arrows B. More specifically, in some embodiments, the carriage 1626 includes a carriage nut 1634 mounted to the lead screw 1622 and secured between the third and fourth layers 1628*c,d*. The outer surface of the lead screw 1622 defines outer helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the drive housing 1614.

As indicated above, the lead screw 1622 and the splines 1624a-c are rotatably mounted to the first and second ends 1618a,b. More specifically, the first end 1618a of the drive housing 1614 may include one or more rotatable drive inputs actuatable to independently drive (rotate) the lead screw 1622 and the splines 1624a-c. In the illustrated embodiment, the drive housing 1614 includes a first drive input 1636a, a second drive input 1636b, a third drive input 1636c (occluded by the shaft 1602, see FIG. 17B), and a fourth drive input 1636d. As described below, each drive input 1636a-d may be matable with a corresponding drive output of an instrument driver such that movement (rotation) of a given drive output correspondingly moves (rotates) the associated drive input 1636a-d and thereby rotates the mated lead screw 1622 or spline 1624a-c. While four drive inputs 1636a-d are depicted, more or less than four may be included in the drive housing 1614 as need requires.

The first drive input 1636a may be operatively coupled to the lead screw 1622 such that rotation (actuation) of the first drive input 1636a correspondingly rotates the lead screw 1622, which causes the carriage nut 1634 and the carriage 1626 to advance or retract along the longitudinal axis $A_1$, depending on the rotational direction of the lead screw 1622. As used herein the phrase "operatively coupled" refers to a coupled engagement, either directly or indirectly, where movement of one component causes corresponding movement of another component. With respect to the first drive input 1636a being operatively coupled to the lead screw 1622, such operative coupling may be facilitated through intermeshed gears (not shown) arranged within the second end 1618a, but could alternatively be facilitated through other mechanical means, such as cables, pulleys, drive rods, belts, direct couplings, etc., without departing from the scope of the disclosure.

The second drive input 1636b may be operatively coupled to the first spline 1624a such that rotation (actuation) of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and thereby open or close the jaws 1610, 1612, depending on the rotational direction of the first spline 1624a.

The third drive input 1636c may be operatively coupled to the second spline 1624b such that rotation (actuation) of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and thereby cause the wrist 1606 to articulate in at least one degree of freedom, depending on the rotational direction of the second spline 1624b.

The fourth drive input 1636d may be operatively coupled to the third spline 1624c such that rotation (actuation) of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the knife at the end effector 1604. Accordingly, rotating the fourth drive input 1636d will correspondingly actuate the third activating mechanism 1638c and thereby cause the knife to advance or retract, depending on the rotational direction of the third spline 1624c.

In the illustrated embodiment, the activating mechanisms 1638a-c may comprise intermeshed gearing assemblies including one or more drive gears driven by rotation of the corresponding spline 1624a-c and configured to drive one or more corresponding driven gears that cause operation of the aforementioned functions of the end effector 1604. It is further contemplated herein, however, that the activating mechanisms 1638a-c may be operated through other types of mechanical cooperation such as, but not limited to, belts or cables.

In some embodiments, the drive housing 1614 may include a shroud 1640 sized to receive and otherwise surround the carriage 1626, the lead screw 1622, and the splines 1624a-c. In the illustrated embodiment, the shroud 1640 comprises a tubular or cylindrical structure having a first end 1642a matable with the first end 1618a of the drive housing 1614, and a second end 1642b matable with the second end 1618b of the drive housing 1614. The carriage 1626, the lead screw 1622, and the splines 1624a-c can all be accommodated within the interior of the shroud 1640, and the carriage 1626 may engage and traverse (ride on) one or more rails 1644 (shown in phantom) fixed to the shroud 1640. The rails 1644 extend longitudinally and parallel to the lead screw 1622 and are sized to be received within corresponding notches 1646 defined on the outer periphery of the carriage 1626 and, more particularly, on the outer periphery of one or more of the carriage layers 1628a-e. As the carriage 1626 translates along the longitudinal axis $A_1$, the rails 1644 help maintain the angular position of the carriage 1626 and assume any torsional loading that might otherwise adversely affect movement or operation of the carriage 1626.

Figure 17A:
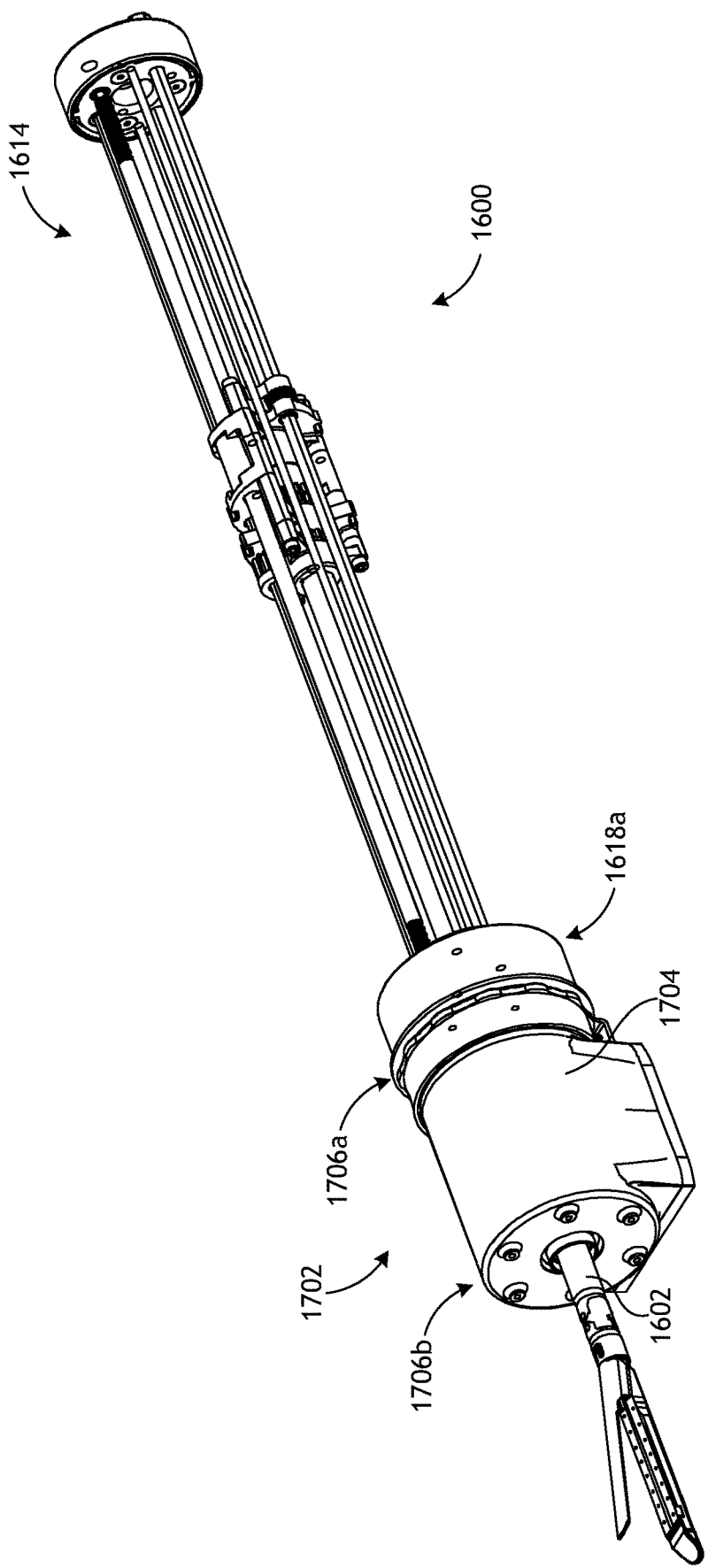
FIG. 17A is an isometric view of the surgical tool of FIG. 16 releasably coupled to an example tool driver, according to one or more embodiments.

FIG. 17A is an isometric view of the surgical tool 1600 releasably coupled to an example instrument driver 1702, according to one or more embodiments. The instrument driver 1702 may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and designed to provide the motive forces required to operate the surgical tool 1600. Unlike the instrument drivers 1102, 1200, however, the shaft 1602 of the surgical tool 1600 extends through and penetrates the instrument driver 1702.

The instrument driver 1702 has a body 1704 having a first or "proximal" end 1706a and a second or "distal" end 1706b opposite the first end 1706a. In the illustrated embodiment, the first end 1706a of the instrument driver 1702 is matable with and releasably coupled to the first end 1618a of the drive housing 1614, and the shaft 1602 of the surgical tool 1600 extends through the body 1704 and distally from the second end 1706b.

Figure 17B:
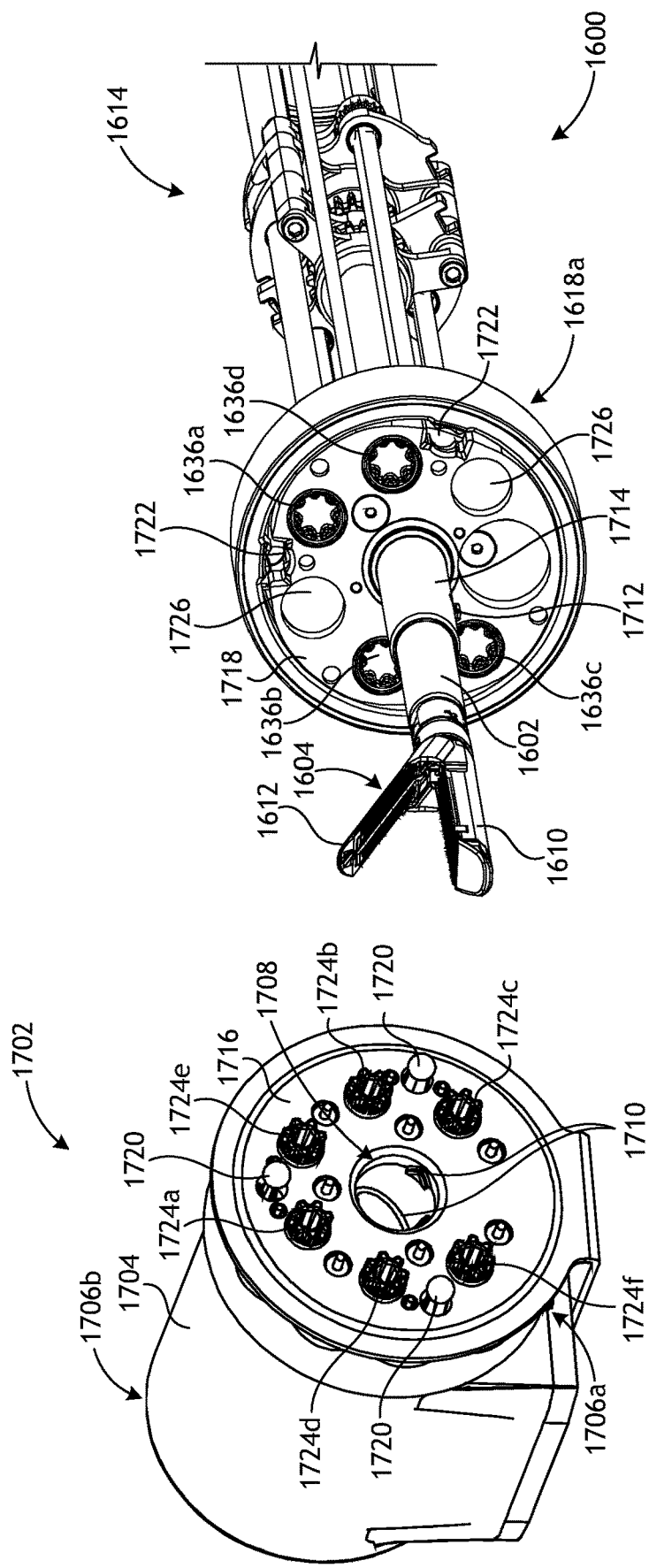
FIG. 17B provides separated isometric end views of the tool driver and the surgical tool of FIG. 17A.

FIG. 17B depicts separated isometric end views of the instrument driver 1702 and the surgical tool 1600 of FIG. 17A. With the jaws 1610, 1612 closed, the shaft 1602 and the end effector 1604 can penetrate the instrument driver 1702 by extending through a central aperture 1708 defined longitudinally through the body 1704 between the first and second ends 1706a,b. To align the surgical tool 1600 with the instrument driver 1702 in a proper angular orientation, one or more alignment guides 1710 may be provided or otherwise defined within the central aperture 1708 and configured to engage one or more corresponding alignment features 1712 provided on the surgical tool 1600. In the illustrated embodiment, the alignment feature 1712 comprises a protrusion or projection defined on or otherwise provided by an alignment nozzle 1714 extending distally from the first end 1618a of the drive housing 1614. In one or more embodiments, the alignment guide 1710 may comprise a curved or arcuate shoulder or lip configured to receive and guide the alignment feature 1712 as the alignment nozzle 1714 enters the central aperture 1708. As a result, the surgical tool 1600 is oriented to a proper angular alignment with the instrument driver 1702 as the alignment nozzle 1714 is advanced distally through the central aperture 1708. In other embodiments, the alignment nozzle 1714 may be omitted and the alignment feature 1712 may alternatively be provided on the shaft 1602, without departing from the scope of the disclosure.

As illustrated, a drive interface 1716 is provided at the first end 1706a of the instrument driver 1702, and a driven interface 1718 is provided at the first end 1618a of the drive housing 1614. The drive and driven interfaces 1716, 1718 may be configured to mechanically, magnetically, and/or electrically couple the drive housing 1614 to the instrument driver 1702. To accomplish this, the drive and driven interfaces 1716, 1718 may provide one or more matable locating features configured to secure the drive housing 1614 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. The features 1720 may be configured to align and mate with the pockets 1722 via an interference or snap fit engagement, for example.

The instrument driver 1702 also includes one or more drive outputs that protrude from the drive interface 1716 to mate with the drive inputs 1636a-d provided at the first end 1618a of the drive housing 1614. More specifically, the instrument driver 1702 includes a first drive output 1724a matable with the first drive input 1636a, a second drive output 1724b matable with the second drive input 1636b, a third drive output 1724b matable with the third drive input 1636c, and a fourth drive output 1724d matable with the fourth drive input 1636d. In some embodiments, as illustrated, the drive outputs 1724a-d may define splines or features designed to mate with corresponding splined receptacles of the drive inputs 1636a-d. Once properly mated, the drive inputs 1636a-d will share axes of rotation with the corresponding drive outputs 1724a-d to allow the transfer of rotational torque from the drive outputs 1724a-d to the corresponding drive inputs 1636a-d. In some embodiments, each drive output 1724a-d may be spring loaded and otherwise biased to spring outwards away from the drive interface 1716. Moreover, each drive output 1724a-d may be capable of partially or fully retracting into the drive interface 1716.

In some embodiments, the instrument driver 1702 may include additional drive outputs, depicted in FIG. 17B as fifth and sixth drive outputs 1724e, 1724f. The fifth and sixth drive outputs 1724e,f may be configured to mate with additional drive inputs (not shown) of the drive housing 1614 to help undertake one or more additional functions of the surgical tool 1600. The drive housing 1614 does not include additional drive inputs matable with the fifth and sixth drive outputs 1724e,f in the illustrated embodiment. Instead, the driven interface 1718 defines corresponding recesses 1726 configured to receive the fifth and sixth drive outputs 1724e,f. In other applications, however, fifth and/or sixth drive inputs could be included in the drive housing 1614 to mate with the fifth and sixth drive outputs 1724e,f, or the surgical tool 1600 might be replaced with another surgical tool having fifth and/or sixth drive inputs, which would be driven by the fifth and/or sixth drive outputs 1724e,f.

While not shown, in some embodiments, an instrument sterile adapter (ISA) may be placed at the interface between the instrument driver 1702 and the surgical tool 1600. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the surgical tool 1600 to the ISA and simultaneously to the instrument driver 1702.

Slipper Clutch Mechanism for Bailout

Figure 18:
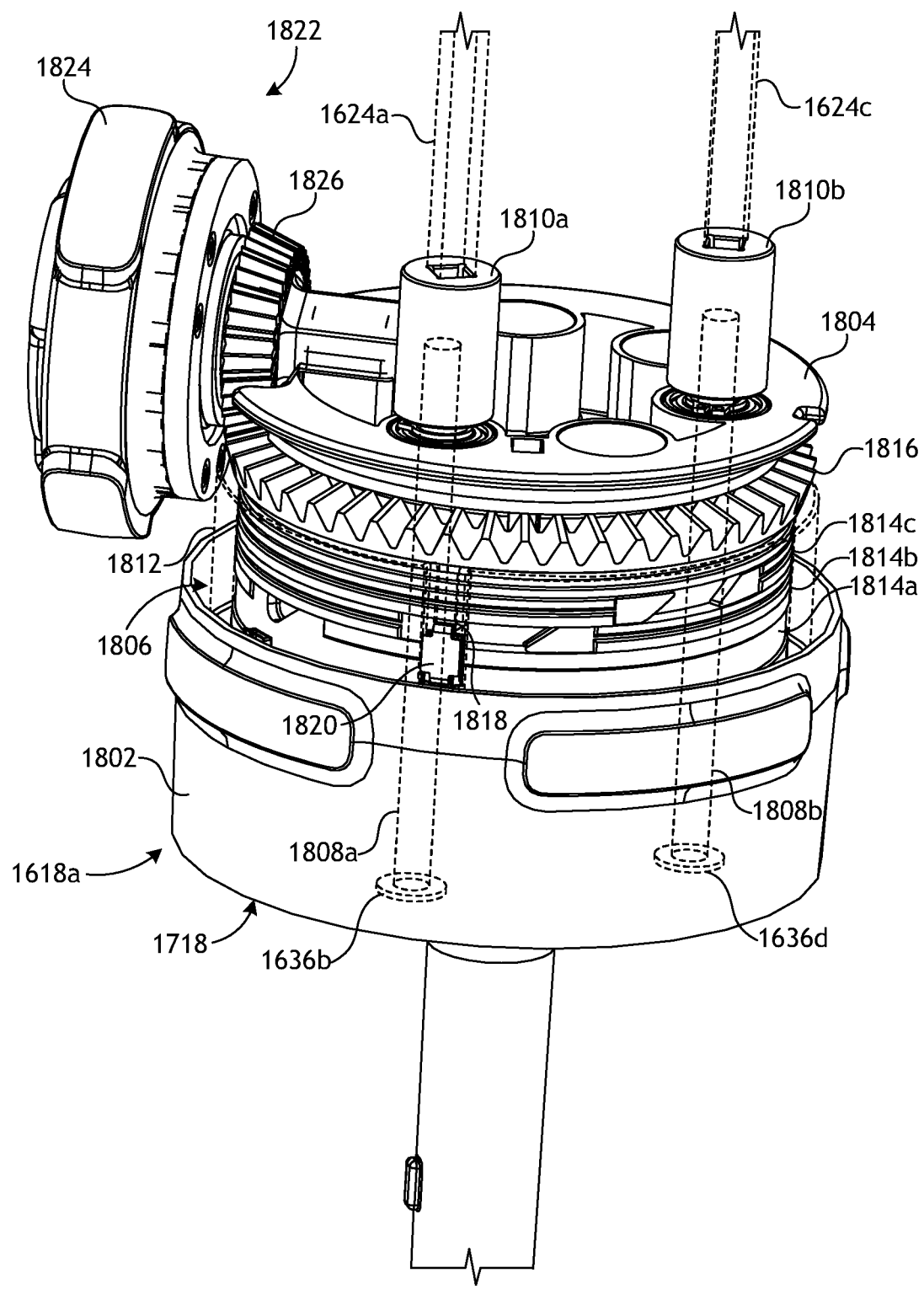
FIG. 18 is an enlarged isometric view of the distal end of the drive housing of FIGS. 16 and 17A-17B, according to one or more embodiments.

FIG. 18 is an enlarged isometric view of the distal end 1618a of the drive housing 1614 of FIGS. 16 and 17A-17B, according to one or more embodiments. As noted above, the distal end 1618a can alternately be referred to as the "handle," and thus may be interchangeably referred to herein as the handle 1618a in the following discussion. As illustrated, the handle 1618a includes a bailout ring 1802, a closure plate 1804, and a slipper clutch mechanism 1806 arranged between the bailout ring 1802 and the closure plate 1804. The bailout ring 1802 is rotatably mounted to the driven interface 1718 and at least partially receives the slipper clutch mechanism 1806. The closure plate 1804 is mounted on top of the slipper clutch mechanism 1806 and is secured to the driven interface 1718 using one or more mechanical fasteners (not shown) that extend longitudinally through the slipper clutch mechanism 1806 and the bailout ring 1802. Securing the closure plate 1804 to the driven interface 1718 helps secure the slipper clutch mechanism 1806 within the handle 1618a for operation.

As indicated above, the second drive input 1636b may be operatively coupled to the first spline 1624a (shown in dashed lines) such that rotation (actuation) of the second drive input 1636b correspondingly rotates the first spline 1624a. In the illustrated embodiment, a first drive shaft 1808a and a first spline coupling 1810a may operatively couple the second drive input 1636b to the first spline 1624a. Operation (rotation) of the second drive input 1636b may correspondingly rotate the first drive shaft 1808a and the first spline coupling 1810a, and thereby cause the first spline 1624a to rotate in the same angular direction. Rotating the first spline 1624a, as mentioned above, may cause the jaws 1610, 1612 (FIGS. 16 and 17B) to open or close, depending on the rotational direction of the first spline 1624a.

Similarly, as also indicated above, the fourth drive input 1636d may be operatively coupled to the third spline 1624c (shown in dashed lines) such that rotation (actuation) of the fourth drive input 1636d correspondingly rotates the third spline 1624c. In the illustrated embodiment, a second drive shaft 1808b and a second spline coupling 1810b may operatively couple the fourth drive input 1636d to the third spline 1624c. Operation (rotation) of the fourth drive input 1636d may correspondingly rotate the second drive shaft 1808b and the second spline coupling 1810b, and thereby cause the third spline 1624c to rotate in the same angular direction. Rotating the third spline 1624c, as mentioned above, may cause the knife at the end effector 1604 (FIGS. 16 and 17B) to advance or retract, depending on the rotational direction of the third spline 1624c.

The slipper clutch mechanism 1806 may be manually actuatable to bail out the surgical tool 1600 (FIG. 16) from various operations or configurations. Bailing out the surgical tool 1600 may prove advantageous, for example, in the event power to the surgical tool 1600 is lost or the surgical tool 1600 is otherwise rendered inoperable. In the illustrated embodiment, the slipper clutch mechanism 1806 may be manually actuatable to translate (e.g., retract) the knife at the end effector 1604 (FIGS. 16 and 17B) and further manually actuatable to open or close the jaws 1610, 1612 (FIGS. 16 and 17B) of the end effector 1604. In other embodiments, however, the slipper clutch mechanism 1806 may be manually actuatable to carry out other bailout procedures including, but not limited to, articulating the end effector 1604 at the wrist 1606 (FIG. 16), opening the jaws 1610, 1612 (without the need of a knob), retracting a biopsy needle, disconnecting electrocautery, opening scissors, releasing a clip, translation of the handle 1618a, decoupling, locking of the insertion drive, or any combination thereof.

In the illustrated embodiment, the slipper clutch mechanism 1806 includes a slip carrier 1812 (shown in phantom), a first or "bailout starter ring" 1814a, a second or "dwell" ring 1814b, a third or "firing/retraction" ring 1814c, and a crown gear 1816, where the rings 1814a-c and the crown gear 1816 are stacked vertically in series and received at least partially within the slip carrier 1812. In operation, the rings 1814a-c may be capable of independently rotating relative to the others, with little or no friction between the adjacent rings 1814a-c. While three rings 1814a-c are included in the illustrated embodiment, more or less than three may alternately be included, without departing from the scope of the disclosure. For example, embodiments are contemplated herein that include only the first and third rings 1814a,c, and omit the second ring 1814b.

The slip carrier 1812 may be at least partially received within the bailout ring 1802. As described in more detail below, the slip carrier 1812 may be operatively coupled to the bailout ring 1802 such that manually rotating the bailout ring 1802 causes the slip carrier 1812 to rotate in the same angular direction and thereby start to manually actuate the slipper clutch mechanism 1806. The slip carrier 1812 defines a vertical slot 1818 and a pin 1820 may be movably (slidably) received within the vertical slot 1818. As the slip carrier 1812 rotates, the pin 1820 may be configured to translate vertically within the vertical slot 1818 to selectively interact with the rings 1814a-c.

In some embodiments, the slipper clutch mechanism 1806 may further include a bailout device 1822 that may be manually operable to open or close the jaws 1610, 1612 (FIGS. 16 and 17B) of the end effector 1604 (FIGS. 16 and 17B). In the illustrated embodiment, for example, the bailout device 1822 comprises a knob 1824 coupled to a drive gear 1826. The drive gear 1826 may be arranged to intermesh with corresponding gear teeth defined on the crown gear 1816. Accordingly, manual rotation (actuation) of the knob 1824 may cause the drive gear 1826 to drive the crown gear 1816 in rotation. As discussed in more detail below, the crown gear 1816 may be operatively coupled to the first drive shaft 1808a such that rotation of the crown gear 1816 correspondingly causes the first drive shaft 1808a to rotate, and thereby rotate the first spline 1624a to open or close the jaws 1610, 1612, depending on the rotational direction of the crown gear 1816.

Figure 19A:
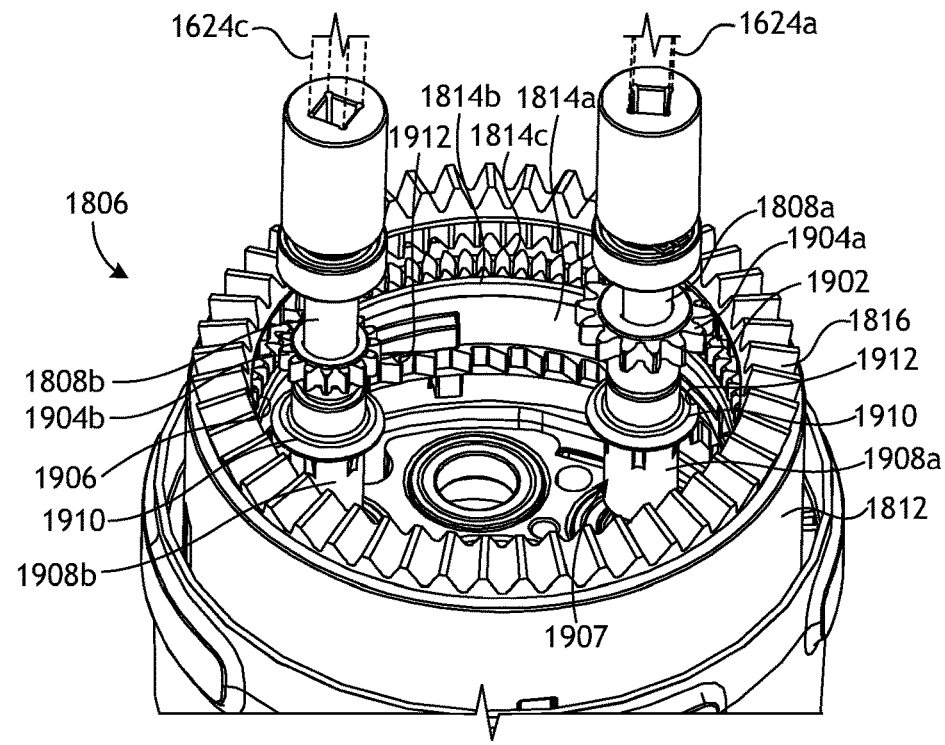
FIG. 19A is an enlarged isometric view of the interior of the slipper clutch mechanism of FIG. 18, according to one or more embodiments.

FIG. 19A is an enlarged isometric view of the interior of the slipper clutch mechanism 1806, according to one or more embodiments. Various internal components and parts are omitted in FIG. 19A to enable viewing of other portions of the slipper clutch mechanism 1806. As illustrated, the rings 1814a-c are stacked vertically in series and received at least partially within the slip carrier 1812, which is received within the bailout ring 1802. The crown gear 1816 may be positioned on top of the firing/retraction ring 1814c and may be configured to slidingly engage the upper surface of the firing/retraction ring 1814c during operation.

More specifically, the crown gear 1816 may provide or otherwise define a series of radial gear teeth 1902 extending about an inner circumference (surface) of the crown gear 1816. A first pinion gear 1904a may be coupled to the first drive shaft 1808a and engageable with the radial gear teeth 1902 of the crown gear 1816 such that movement (rotation) of the crown gear 1816 correspondingly drives the first pinion gear 1904a, which causes the first drive shaft 1808a to rotate. Accordingly, rotating the crown gear 1816, such as through manual rotation (actuation) of the knob 1824 (FIG. 18), may cause the first drive shaft 1808a to rotate and thereby rotate the first spline 1624a (shown in dashed lines) to open or close the jaws 1610, 1612, depending on the rotational direction of the crown gear 1816.

The firing/retraction ring 1814c may also provide or otherwise define a series of radial gear teeth 1906 engageable with a second pinion gear 1904b coupled to the second drive shaft 1808b. As the firing/retraction ring 1814c rotates, such as through actuation (rotation) of the slipper clutch mechanism 1806, the second drive shaft 1808b will be correspondingly driven in rotation via engagement of the second pinion gear 1904b and the radial gear teeth 1906, and rotating the second drive shaft 1808b will rotate the third spline 1624c (shown in dashed lines) and thereby translate (e.g., retract) the knife at the end effector 1604 (FIGS. 16 and 17B).

In some embodiments, the slipper clutch mechanism 1806 may further include a decoupling mechanism 1907, which may provide first and second decoupling plunger caps 1908a and 1908b movably mounted to the first and second drive shafts 1808a,b, respectively. Each decoupling plunger cap 1908a,b may provide a radial flange 1910 engageable with one or more ramps 1912 (two shown) defined on the inner circumference of the bailout starter ring 1814a. The decoupling plunger caps 1908a,b may be spring loaded and capable of moving (transitioning) along the corresponding drive shafts 1808a,b as acted upon by the ramps 1912. More specifically, as the bailout starter ring 1814a rotates, such as through actuation (rotation) of the slipper clutch mechanism 1806, the ramps 1912 will engage the radial flanges 1910 and thereby force the decoupling plunger caps 1908a,b downward (distally) relative to the corresponding drive shafts 1808a,b. Each decoupling plunger cap 1908a,b may provide a distally-extending shaft (not shown) engageable with the corresponding second and fourth drive outputs 1724b,d (FIG. 17B) mated with the second and fourth drive inputs 1636b,d (FIGS. 16, 17B, and 18), respectively. Forcing the decoupling plunger caps 1908a,b downward (distally) will correspondingly drive the distally-extending shafts into engagement with the respective drive outputs 1724b,d, and thereby decouple the drive outputs 1724b,d from the drive inputs 1636b,d. As will be appreciated, this will decouple the drive output 1724b,d motors from the drive shafts 1808a,b, which allows the splines 1624a,c to be back driven without resistance of the motors as the slipper clutch mechanism 1806 continues to actuate (rotate). Once the decoupling plunger caps 1908a,b are pressed down, they may remain held in position during and after a bailout sequence has been executed.

Figure 19B:
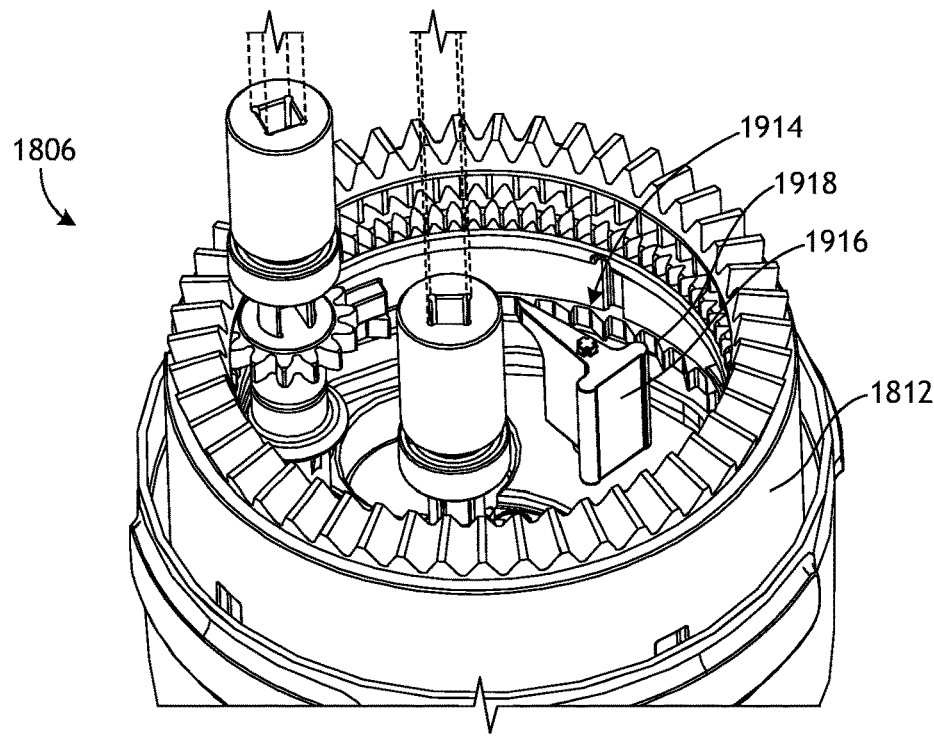
FIG. 19B is another enlarged isometric view of the interior of the slipper clutch mechanism of FIG. 18, according to one or more embodiments.

FIG. 19B is another enlarged isometric view of the interior of the slipper clutch mechanism 1806, according to one or more embodiments. Again, various internal components and parts are omitted in FIG. 19B to enable viewing of other portions of the slipper clutch mechanism 1806. In some embodiments, the slipper clutch mechanism 1806 may include an anti-reverse mechanism 1914 that allows the slipper clutch mechanism 1806 to be actuated (rotated) in one angular direction (e.g., clockwise), while simultaneously preventing the slipper clutch mechanism 1806 from being actuated (rotated) in the opposite angular direction (e.g., counter-clockwise).

In the illustrated embodiment, the anti-reverse mechanism 1914 may include a spring-actuated pawl 1916 engageable with ratchet teeth 1918 defined on an inner circumferential surface of the slip carrier 1812. In example operation, as the slipper clutch mechanism 1806 is actuated and the slip carrier 1812 is thereby rotated in a first angular direction (e.g., clockwise), the pawl 1916 will ratchet along the ratchet teeth 1918 defined on the slip carrier 1812. In some embodiments, ratcheting the pawl 1916 on the ratchet teeth 1918 will provide audible and/or tactile feedback to the user, thus providing the user with positive indication that the slipper clutch mechanism 1806 is properly operating. The audible and/or tactile feedback may prove advantageous for user ease and experience, such as by ensuring a user that the slipper clutch mechanism 1806 is being actuated in the proper direction, which could save time to bailout by eliminating confusion. The angle of the ratchet teeth 1918 and the orientation of the pawl 1916, however, prevent the slip carrier 1812 from being rotated in a second direction (e.g., counter-clockwise) opposite first angular direction, which may be important in preventing a user from inadvertently advancing the knife at the end effector 1604 (FIGS. 16 and 17B), for example.

Figure 20:
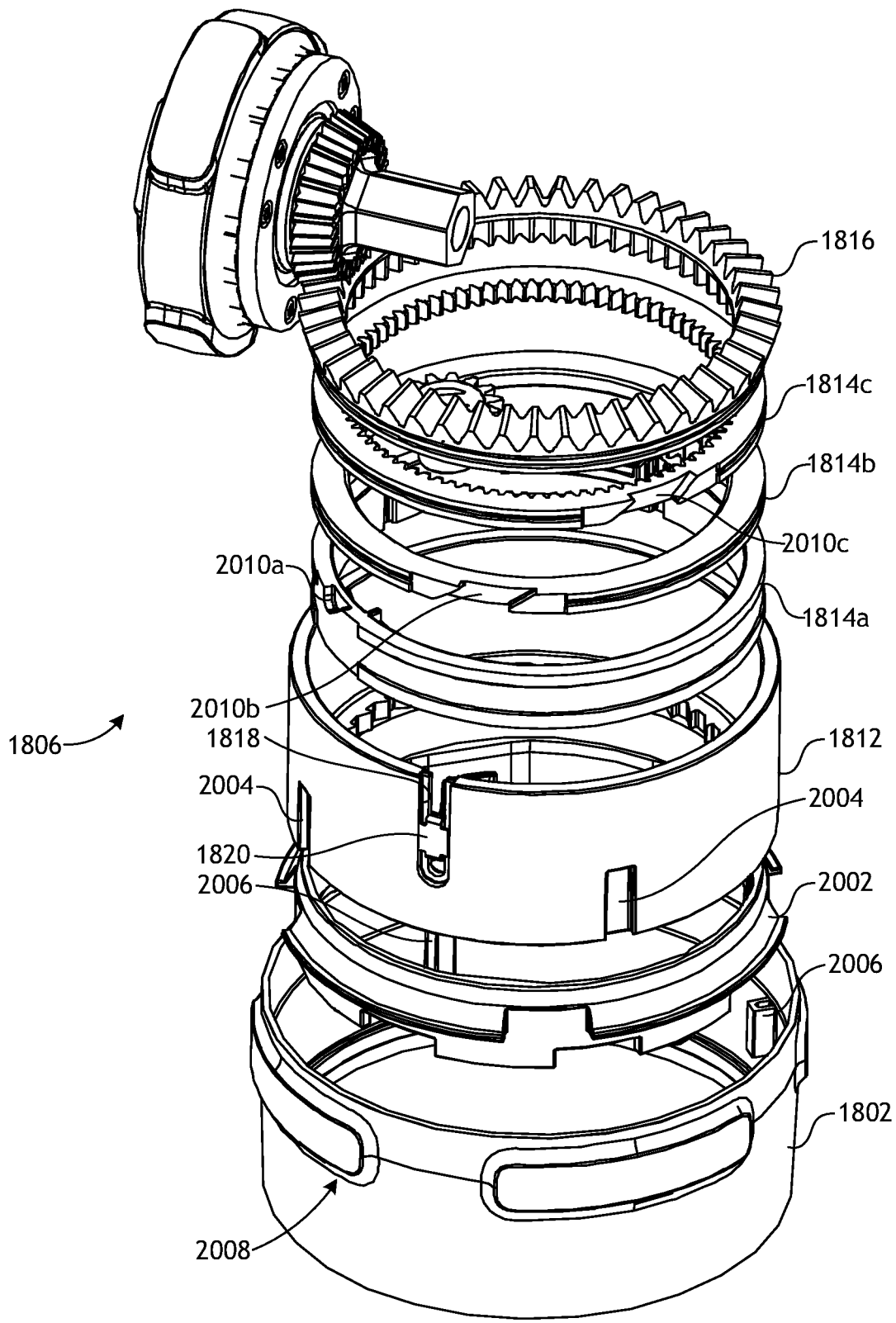
FIG. 20 is an exploded isometric view of the slipper clutch mechanism of FIG. 18, according to one or more embodiments.

FIG. 20 is an exploded isometric view of the slipper clutch mechanism 1806, according to one or more embodiments. In the illustrated embodiment, the slipper clutch mechanism 1806 may further include a latch ring 2002 sized to be received within the bailout ring 1802. Portions of the latch ring 2002 may extend past the driven interface 1718 (FIGS. 17B and 18) to help couple the surgical tool 1600 (FIGS. 16 and 17B) to the instrument driver 1702 (FIGS. 17A-17B). The latch ring 2002 may be spring loaded and manually actuatable to attach/detach the surgical tool 1600 to/from the instrument driver 1702. More specifically, a user may manually grasp and push (move) the bailout ring 1802 proximally relative to the slipper clutch mechanism 1806, which will correspondingly move the latch ring 2002 in the same direction and compress one or more springs (not shown) interposing portions of the bailout ring 1802 and the latch ring 2002. As the latch ring 2002 moves proximally, the driven interface 1718 may be detached from the drive interface 1716 (FIG. 17B) of the instrument driver 1702, and thus release the surgical tool 1600 from the instrument driver 1702.

In some embodiments, the slip carrier 1812 may be received within the bailout ring 1802 in a mated relationship. More specifically, the slip carrier 1812 may define one or more indentations 2004 (two visible) about its outer periphery, and the bailout ring 1802 may define one or more corresponding protrusions 2006 (two partially visible) about its inner circumference. Mating the protrusions 2006 with the indentations during assembly of the slipper clutch mechanism 1806 may rotationally lock the slip carrier 1812 to the bailout ring 1802 such that manually rotating the bailout ring 1802 will correspondingly rotate the slip carrier 1812 in the same angular direction. As discussed herein, rotating the slip carrier 1812 causes the slipper clutch mechanism 1806 to actuate (operate).

In some embodiments, the outer periphery (circumference) of the bailout ring 1802 may provide or otherwise define a gripping interface 2008. The gripping interface 2008 may comprise a feature or structure that may be gripped or grasped by a user to manually manipulate the bailout ring 1802 (e.g., rotating or axially moving the bailout ring 1802). In the illustrated embodiment, the gripping interface 2008 comprises one or more arcuate projections extending radially outward from the outer circumference of the bailout ring 1802, but could alternatively comprise any other type of feature or structure engageable or graspable by a user's hand.

The rings 1814a-c may each provide suitable ring drive geometry capable of interacting with the pin 1820 to rotate the corresponding ring 1814a-c when the pin is received at the ring 1814a-c. In the illustrated embodiment, the rings 1814a-c may each provide or define an interface at one or more locations about its outer circumference. More specifically, the bailout starter ring 1814a provides a first interface 2010a, the dwell ring 1814b provides a second interface 2010b, and the firing/retraction ring 1814c provides a third interface 2010c. In some embodiments, for example, each interface 2010a-c may comprise a depression or detent defined in the outer periphery of the corresponding ring 1814a-c. The second and third interfaces 2010b,c may further extend between the top and bottom surfaces of the rings 1814b,c. The interfaces 2010a-c may be sized to receive a portion of the pin 1820 slidably received within the vertical slot 1818 of the slip carrier 1812. As the slip carrier 1812 rotates about the tool axis during manual actuation of the slipper clutch mechanism 1806, the pin 1820 may be configured to sequentially and successively locate each interface 2010a-c. Upon locating an interface 2010a-c, the pin 1820 translates vertically within the vertical slip 1816 to thereby enters the given interface 2010a-c. The crown gear 1816 does not provide an interface and thereby acts as a ceiling or upper stop to the pin 1820 and otherwise prevents the pin 1820 from moving proximally past the firing/retraction ring 1814c.

In some embodiments, as illustrated, the interfaces 2010a-c may be ramped or angled. In such embodiments, engaging the pin 1820 against the corresponding ramped interface 2010a-c may urge the pin 1820 to translate vertically within the slot 1818. In other embodiments, however, the interfaces 2010a-c may comprise straight, vertical slots. In such embodiments, the pin 1820 may need to be driven, pushed, or pulled through the vertical slot 1818 at each interface 2010a-c to bypass the corresponding ring 1814a-c.

Figure 21A:
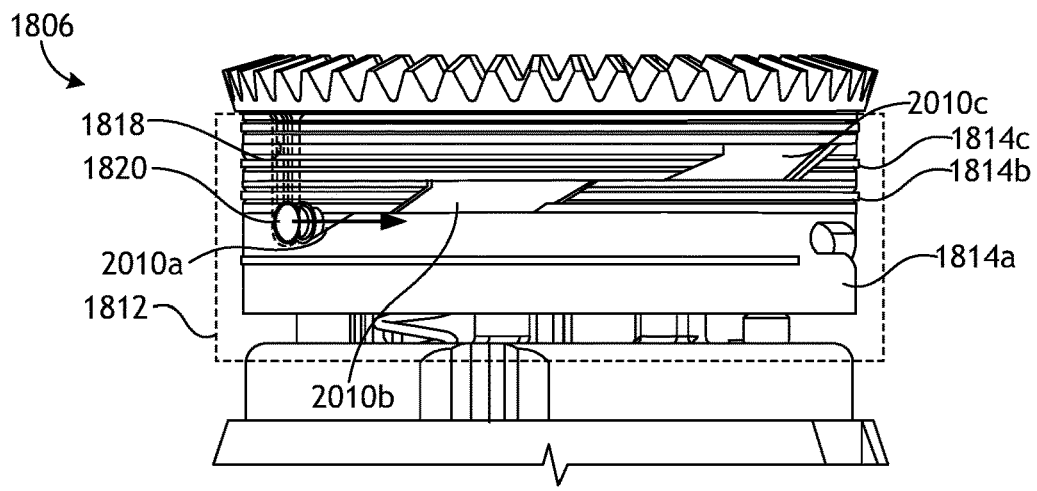
FIGS. 21A-21C are schematic side views of the slipper clutch mechanism of FIG. 18 demonstrating example operation, according to one or more embodiments.
Figure 21B:
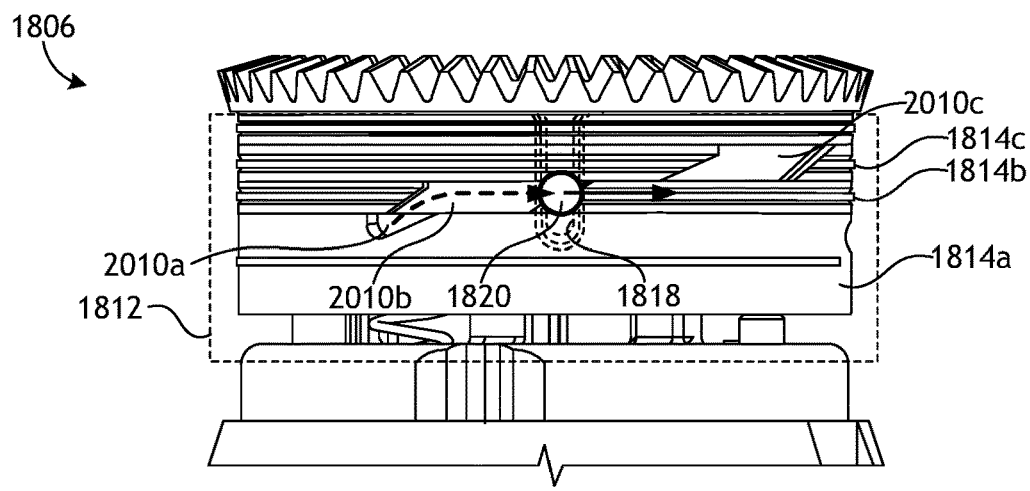

FIGS. 21A-21B are schematic side views of the slipper clutch mechanism 1806 demonstrating example operation thereof, according to one or more embodiments. As mentioned above, the slipper clutch mechanism 1806 may be manually actuatable to bail out the surgical tool 1600 (FIG. 16) from various operations or configurations. In one embodiment, for example, the slipper clutch mechanism 1806 is manually actuatable to translate (e.g., retract) the knife at the end effector 1604 (FIGS. 16 and 17B) and/or open or close the jaws 1610, 1612 (FIGS. 16 and 17B) of the end effector 1604. However, the slipper clutch mechanism 1806 may be alternately configured to carry out other bailout procedures, without departing from the scope of the disclosure.

In example operation, the slip carrier 1812 (shown in phantom) may be rotated (e.g., clockwise) to actuate (operate) the slipper clutch mechanism 1806. More specifically, as discussed above, the slip carrier 1812 may be received within and otherwise mated to the bailout ring 1802 (FIGS. 18 and 20), and manually rotating the bailout ring 1802 will correspondingly rotate the slip carrier 1812 in the same angular direction. Moreover, as the slip carrier 1812 rotates, the pin 1820 may be able to traverse the vertical slot 1818 as the pin 1820 sequentially locates and is received within successive interfaces 2010b,c of the dwell and firing/retraction rings 1814b,c. Translation (movement) of the pin 1820 to successive interfaces 2010b-c allows the pin 1820 to "clutch" from one ring 1814a-c to the next, and can be timed to advance from ring to ring in a known process.

Furthermore, as the slip carrier 1812 rotates, the anti-reverse mechanism 1914 (FIG. 19B) may operate to provide audible and/or tactile feedback to the user as the pawl 1916 (FIG. 19B) ratchets along the ratchet teeth 1918 (FIG. 19B) of the slip carrier 1812. The anti-reverse mechanism 1914 may also prevent the slip carrier 1812 from being back-rotated in the opposite angular direction, thus ensuring that the user is unable to manually drive against the drive motors of the instrument driver 1702 (FIGS. 17A-17B).

Referring first to FIG. 21A, the slip carrier 1812 is rotated (e.g., clockwise) to commence actuation (operation) of the slipper clutch mechanism 1806. The pin 1820 is received within the first interface 2010a of the bailout starter ring 1814a and, consequently, will cause the bailout starter ring 1814a to rotate in the same angular direction. The bailout starter ring 1814a may be rotated relative to the dwell and firing/retraction rings 1814b,c, which remain stationary. The pin 1820 is prevented from moving upward within the vertical slot 1818 until locating the second interface 2010b of the dwell ring 1814b.

As discussed above, as the bailout starter ring 1814a rotates, the ramps 1912 (FIG. 19A) provided on the inner circumference of the bailout starter ring 1814a will engage and force the radial flanges 1910 (FIG. 19A) provided by the decoupling plunger caps 1908a,b (FIG. 19A) downward and thereby decouple the drive outputs 1724b,d (FIG. 17B) from the corresponding drive inputs 1636b,d (FIG. 17B). This may prove advantageous in decoupling the motors that drive the drive outputs 1724b,d from the corresponding drive shafts 1808a,b (FIGS. 18 and 19A), thus allowing the splines 1624a,c (FIGS. 16, 18, and 19A) to be back driven without fighting against the resistance of the drive motors.

In FIG. 21B, the slip carrier 1812 and the bailout starter ring 1814a have rotated a sufficient angular distance to allow the pin 1820 to locate and be received within the second interface 2010b provided by the dwell ring 1814b. Upon locating the second interface 2010b, the pin 1820 is able to move vertically within the vertical slot 1818, and thus exit the first interface 2010a. With the pin 1820 received within the second interface 2010b, continued rotation of the slip carrier 1812 will cause the dwell ring 1814b to rotate relative to the bailout starter ring 1814a and the firing/retraction ring 1814c. The dwell ring 1814b may be rotated until locating the third interface 2010c provided by the firing/retraction ring 1814c. In some embodiments, the dwell ring 1814b may be configured to time the rotation to link to the firing/retraction ring 1814c. In at least one embodiment, however, the dwell ring 1814b may be omitted and the pin 1820 may transition from the bailout starter ring 1814a directly to the firing/retraction ring 1814c, without departing from the scope of the disclosure. In yet other embodiments, the slipper clutch mechanism 1806 may include multiple dwell rings interposing the bailout starter ring 1814a and the firing/retraction ring 1814c or otherwise included at any position or configuration along the stack of rings 1814a-c. In such embodiments, the multiple dwell rings may be configured to provide predetermined angular movement of the slip carrier 1812 until engaging a succeeding ring.

Figure 21C:
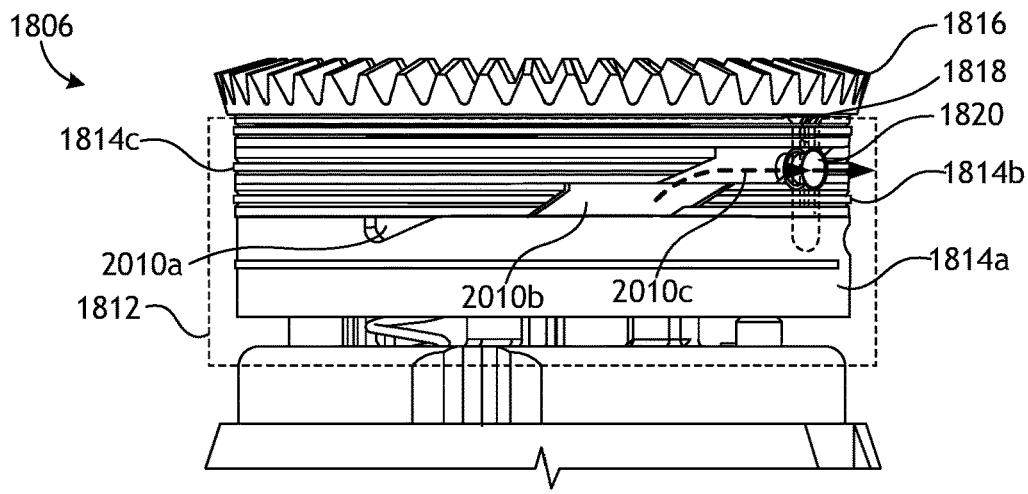

In FIG. 21C, the slip carrier 1812 and the dwell ring 1814b have rotated a sufficient angular distance to allow the pin 1820 to locate and be received within the third interface 2010c provided by the firing/retraction ring 1814c. Upon locating the third interface 2010c, the pin 1820 is able to move vertically within the vertical slot 1818, and thus exit the second interface 2010b. With the pin 1820 received within the third interface 2010c, continued rotation of the slip carrier 1812 will cause the firing/retraction ring 1814c to rotate relative to the bailout starter and dwell rings 1814a,b. As the crown gear 1816 does not provide an interface, the crown gear 1816 may act as a ceiling to the pin 1820 and otherwise prevent the pin 1820 from moving proximally past the firing/retraction ring 1814c and otherwise out of the third interface 2010c.

As mentioned above, rotating the firing/retraction ring 1814c may cause the second drive shaft 1808b (FIGS. 18 and 19A) to rotate and thereby rotate the third spline 1624c (FIGS. 18 and 19AB), which translates (e.g., retracts) the knife at the end effector 1604 (FIGS. 16 and 17B). In other embodiments, however, the slipper clutch mechanism 1806 may alternately be configured such that rotating the firing/retraction ring 1814c may alternately open or close the jaws 1610, 1612 (FIGS. 16 and 17B) of the end effector 1604. In such embodiments, actuating (operating) the bailout device 1822 (FIG. 18) to rotate the crown gear 1816 may alternately translate (e.g., retract) the knife at the end effector 1604, without departing from the scope of the disclosure.

Latch Lock Defeat with Slipper Ring Bailout

Figure 22A:
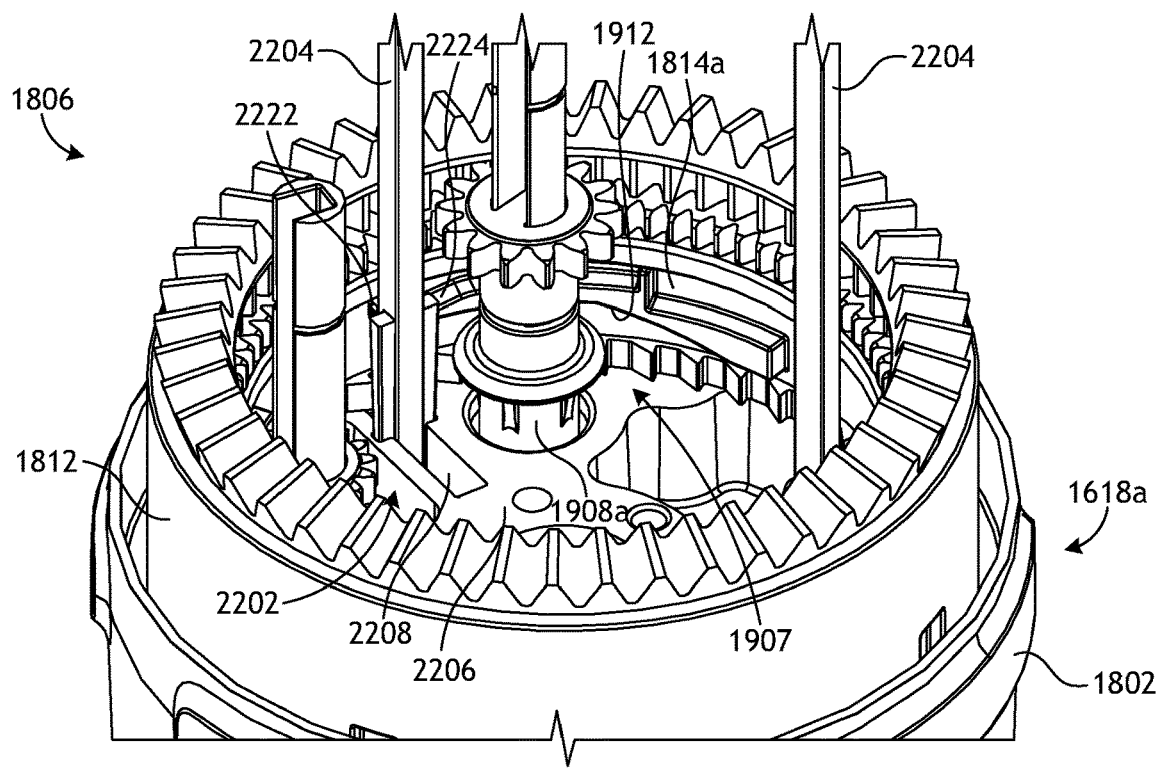
FIG. 22A is another enlarged isometric view of the interior of the slipper clutch mechanism of FIG. 18, according to one or more embodiments.

FIG. 22A is another enlarged isometric view of the interior of the slipper clutch mechanism 1806, according to one or more embodiments. Again, various internal components and parts are omitted in FIG. 22A to enable viewing of other portions of the slipper clutch mechanism 1806. In some embodiments, the slipper clutch mechanism 1806 may further include a latch lock defeat mechanism 2202 operable to help manually release the surgical tool 1600 (FIGS. 16 and 17A-17B) from the instrument driver 1702 (FIGS. 17A-17B).

As illustrated, the latch lock defeat mechanism 2202 may include one or more lifters 2204 (two shown) movably attached to a column 2206 and extending proximally from the handle 1618a. In some embodiments, the lifters 2204 extend to and are coupled to the second end 1618b (FIG. 16) of the surgical tool 1600. The column 2206 may be arranged within the bailout ring 1802 and at least partially arranged within the slip carrier 1812 and adjacent the driven interface 1718 (FIGS. 17B and 18) of the handle 1618a. The distal end of each lifter 2204 may be received within a corresponding pocket 2208 (one visible) defined in the column 2206.

Figure 22B:
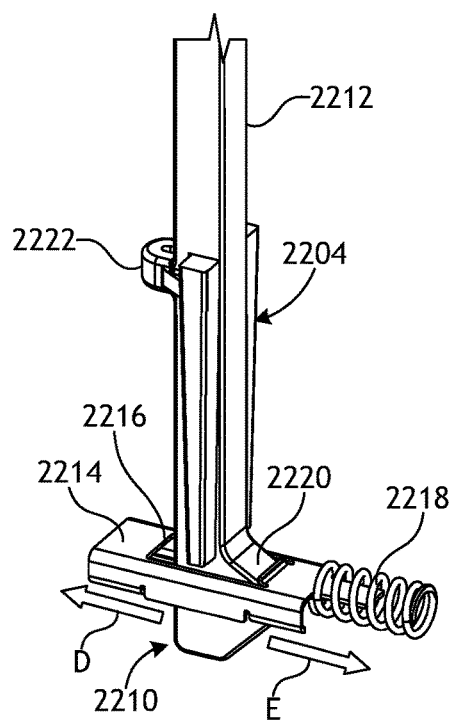
FIG. 22B is an isometric view of an example lifter, according to one or more embodiments.

FIG. 22B depicts an enlarged isometric view of an example lifter 2204, according to one or more embodiments. As illustrated, the lifter 2204 may include a foot 2210 and a lifter shaft 2212 that extends from the foot 2210. The foot 2210 may be received within the pocket 2208 (FIG. 22A) of the column 2206 (FIG. 22A), and a locking tab 2214 may also be arranged within the pocket 2208 to prevent the foot 2210 from exiting the pocket 2208. More specifically, the lifter shaft 2212 may extend through an aperture 2216 defined by the locking tab 2214, but the foot 2210 may be too large to extend through the aperture 2216, thus securing the foot 2210 within the pocket 2008. Consequently, any proximal movement of the lifter 2204 tending to pull the lifter 2204 out of the pocket 2208 will be resisted by the locking tab 2214.

The foot 2210 may be spring-biased 2218 within the pocket 2208 (FIG. 22A) of the column 2206 (FIG. 22A) and thereby naturally urge the locking tab 2214 toward a latched position. In the latched position, the locking tab 2214 extends radially out of the pocket 2208 in the direction D and thereby inhibits unlatching of the handle 1618a (FIG. 22A) from the instrument driver 1702 (FIGS. 17A-17B), as described in more detail below.

As illustrated, a top 2220 of the foot 2210 may be angled and otherwise slanted. Actuating the slipper clutch mechanism 1806 (FIG. 22A) may cause the lifter 2204 to move proximally (up), which correspondingly draws the angled top 2220 of the foot 2210 in the same direction. As the foot 2210 moves proximally, the angled top 2220 acts on the locking tab 2214 at the aperture 2216 and urges the locking tab 2214 toward a released position, as indicated by the arrow E. More specifically, moving the foot 2210 proximally urges the angled top 2220 against the locking tab 2214, which correspondingly urges the locking tab 2214 radially inward and further into the pocket 2208 (FIG. 22A) in the direction E opposite the direction D. As the locking tab 2214 moves radially inward E, the spring 2218 will be compressed within the pocket 2208.

Figure 22C:
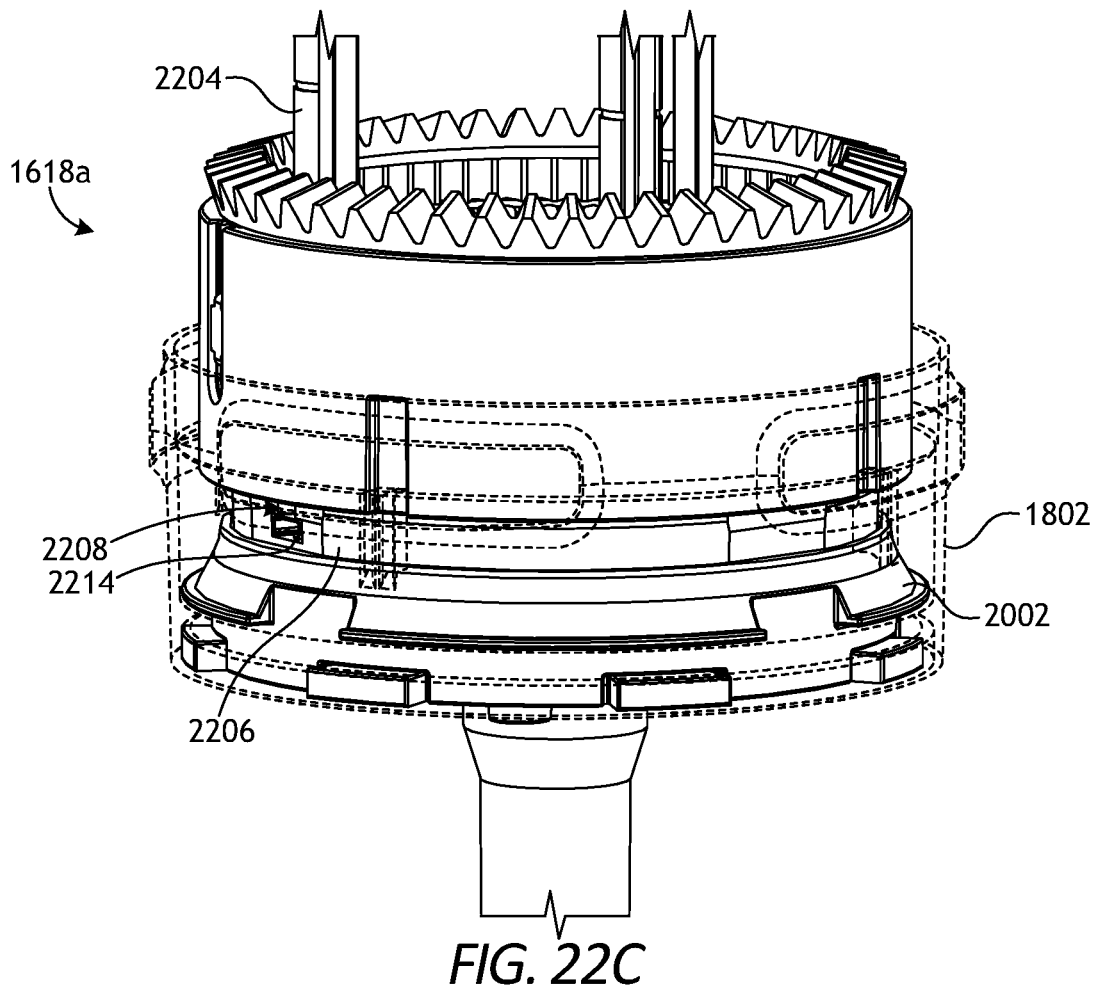
FIG. 22C is a side view of the handle of FIG. 22A.

FIG. 22C is a side view of the handle 1618a of FIG. 22A. The bailout ring 1802 is shown in phantom (dashed lines) to enable viewing of various internal parts of the handle 1618a. More specifically, a radial end of one of the pockets 2208 defined in the column 2006 is visible, and the locking tab 2214 of one of the lifters 2204 can be seen within the pocket 2208. In the illustrated embodiment, the locking tab 2214 is in the released position, where the locking tab 2214 is stowed within the pocket 2208 and otherwise does not extend radially out of the pocket 2208. In this position, the bailout ring 1802 may be manually actuated upward to act on the latch ring 2002, and the latch ring 2002 may correspondingly move upward to release the handle 1618a from the instrument driver 1702 (FIGS. 17A-17B), as generally described above. When the locking tab 2214 is in the latched position, however, the locking tab 2214 will extend radially out from the pocket 2008 and thereby prevent the latch ring 2002 from moving upward (axially) to detach the surgical tool 1600 (FIGS. 16 and 17A-17B) from the instrument driver 1702.

Referring again to FIG. 22A, each lifter 2204 may provide or otherwise define a lateral tab 2222 (partially visible in FIG. 22A, best seen in FIG. 22B). The lateral tab 2222 may be engageable with a corresponding ramp 2224 (one visible) defined on the inner circumference of the bailout starter ring 1814a. As the bailout starter ring 1814a rotates, such as through actuation (rotation) of the slipper clutch mechanism 1806, the ramp 2224 will engage the lateral tab 2222 and thereby urge the lifters 2204 proximally (up) relative to the handle 1618a. As the lifters 2204 move proximally, the corresponding locking tabs 2214 (FIGS. 22B-22C) are moved from the latched position to the released position, as described above.

Figure 22D:
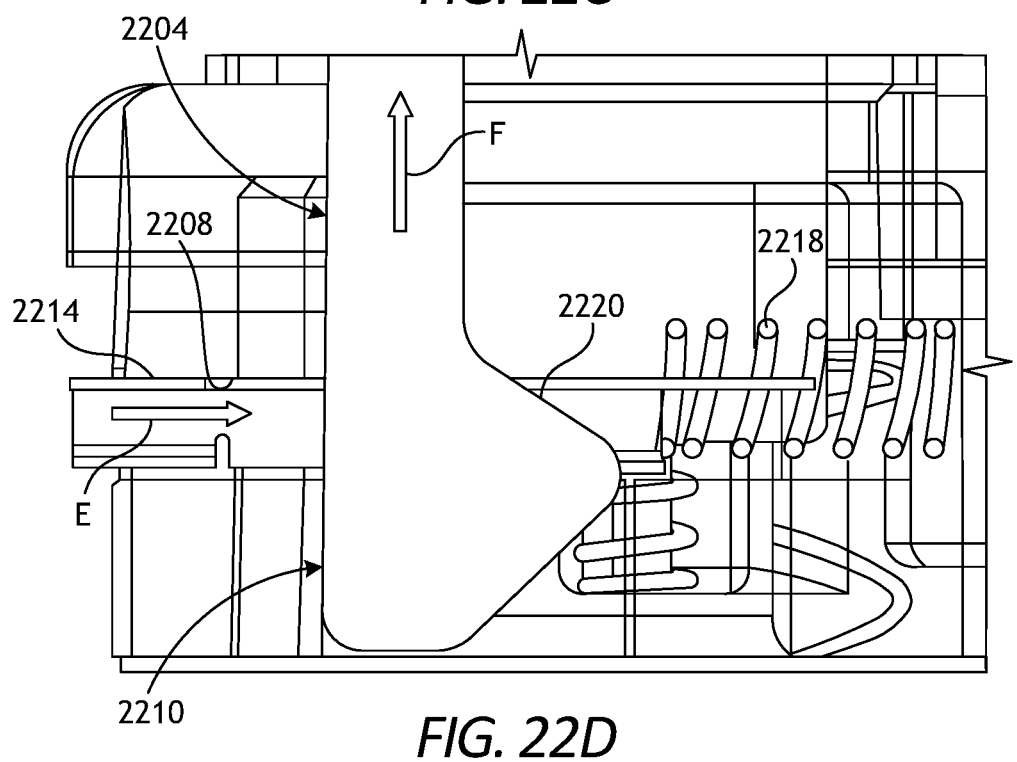
FIG. 22D is an enlarged side view of example operation of the lifter of FIGS. 22A-22B.

FIG. 22D is an enlarged side view of the lifter 2204 depicting example operation, according to one or more embodiments. The lifter 2204 is depicted in FIG. 22D in the latched position, where the locking tab 2214 extends radially out of the pocket 2008. As the lifter 2204 is urged proximally, as shown by the arrow F, the top 2220 of the foot 2210 is moved in the same direction F, which acts on the locking tab 2214. Because of the angled or tapered surface of the top 2220, the locking tab 2214 is urged radially inward in the direction E and to the released position. As the locking tab 2214 is moved further (deeper) into the pocket 2208 to the released position, the spring 2218 becomes progressively compressed.

Referring once again to FIG. 22A, in some embodiments, the decoupling mechanism 1907 and the latch lock defeat mechanism 2202 may be distributed about the circumference of the handle 1618a. More specifically, the ramps 1912 engageable with the decoupling plunger caps 1908a,b (only the first decoupling plunger cap 1908a visible) and the ramps 2222 engageable with the lateral tabs 2222 of the lifters 2204 may be distributed around the circumference of the bailout starter ring 1814a such that the ramps 1912 and the ramps 2222 engage their targets at different angular orientations of the bailout starter ring 1814a. As will be appreciated, this may minimize peak load from the user.

Figure 22E:
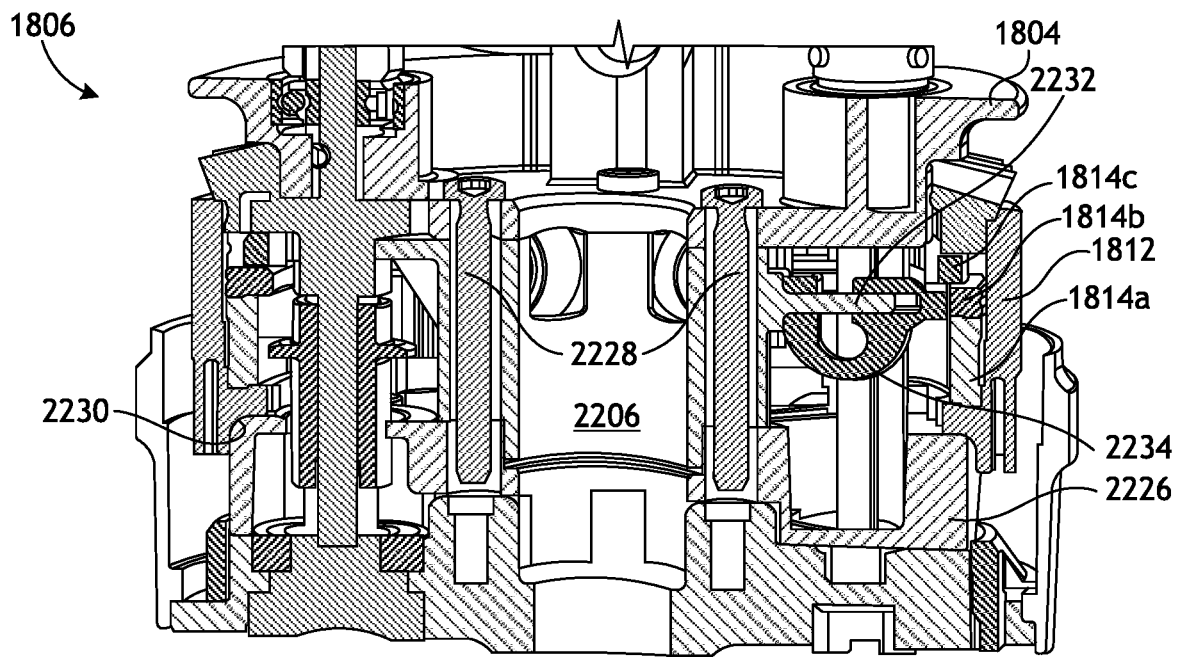
FIG. 22E is a cross-sectional side view of the slipper clutch mechanism of FIG. 18, according to one or more embodiments.

FIG. 22E is a cross-sectional side view of the slipper clutch mechanism 1806, according to one or more embodiments. As illustrated, the closure plate 1804 may be coupled to a base housing 2226 with one or more mechanical fasteners 2228 and the slip carrier 1812 may be arranged concentrically to ride (slidably rotate) upon the base housing 2226 at a rounded interface 2230. In other embodiments, however, the slip carrier 1812 may have rolling contact against the base housing 2226, such as via one or more bearings or rolling elements arranged at the interface. Moreover, the column 2206 may interpose the closure plate 1804 and the base housing 2226.

In some embodiments, the column 2206 may provide or otherwise define one or more guide bars 2232 (one shown) extending laterally from the column 2206. A compliant member 2234 may mate with the guide bar 2232 and extend to contact a portion of one of the rings 1814a-c. In the illustrated embodiment, the compliant member 2234 extends to contact the dwell ring 1814b, but could alternatively be configured to contact the bailout starter ring 1814a or the firing/retraction ring 1814c, without departing from the scope of the disclosure.

Figure 22F:
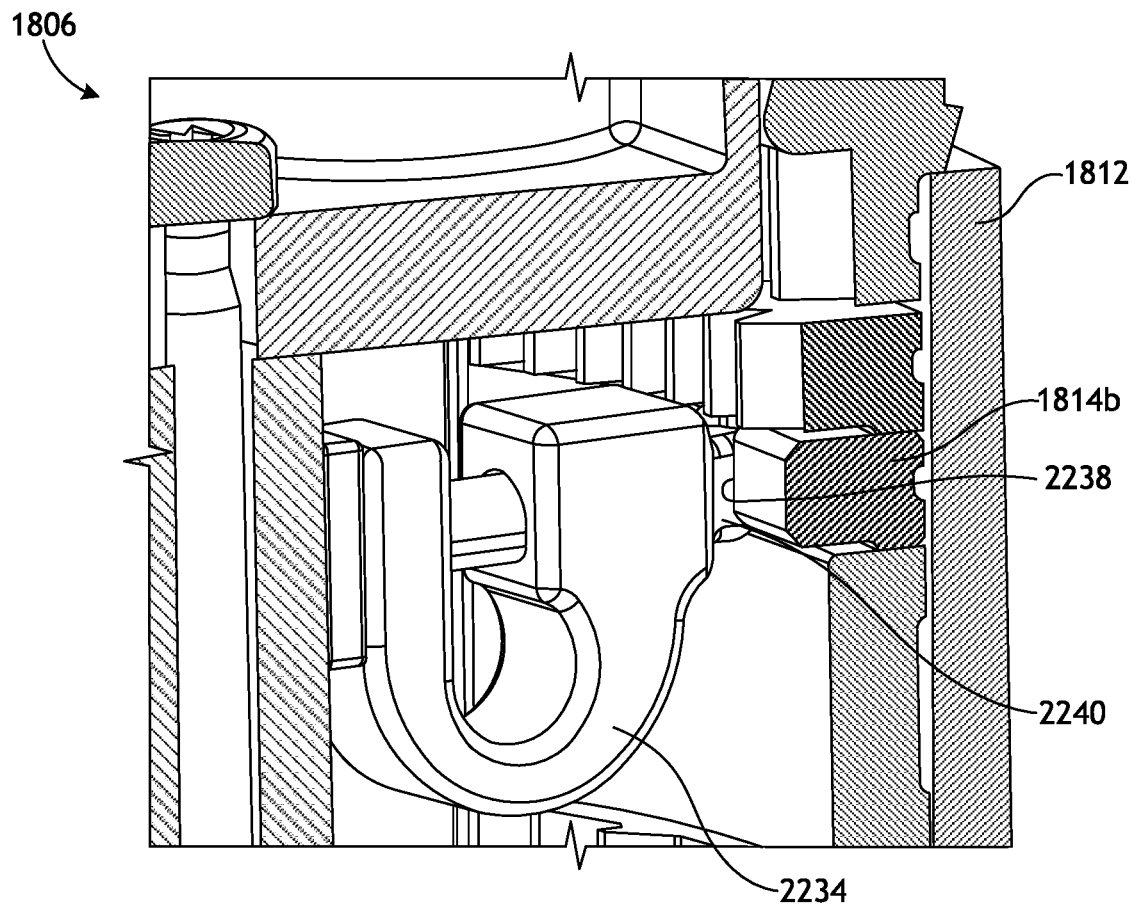
FIG. 22F is an enlarged cross-sectional side view of a portion of the slipper clutch mechanism of FIG. 22E, according to one or more embodiments.

FIG. 22F is an enlarged cross-sectional side view of a portion of the slipper clutch mechanism 1806, according to one or more embodiments. As illustrated, the compliant member 2234 may be configured to engage an inner surface of the dwell ring 1814b. In some embodiments, the inner surface of the dwell ring 1814b may define one or more detents 2238, and the compliant member 2234 may provide or define a projection 2240 configured to locate and be seated within the detent 2238. Locating the projection 2240 within the detent 2238 ensures that the dwell ring 1814b stays stationary until the slipper clutch mechanism 1806 is actuated and the pin 1820 (FIGS. 20 and 21A-21C) has exited the first interface 2010a (FIGS. 20 and 21A) and has transitioned to engage the second interface 2010b. Locating the projection 2240 within the detent 2238 may geometrically control the stroke of the compliant member 2234. Upon rotating the slip carrier 1812, as generally described herein, the compliant member 2234 may flex and allow the projection 2240 to be urged out of the detent 2238 as the dwell ring 1814b begins to rotate. In some cases, this may provide tactile feedback to the user.

Figure 22G:
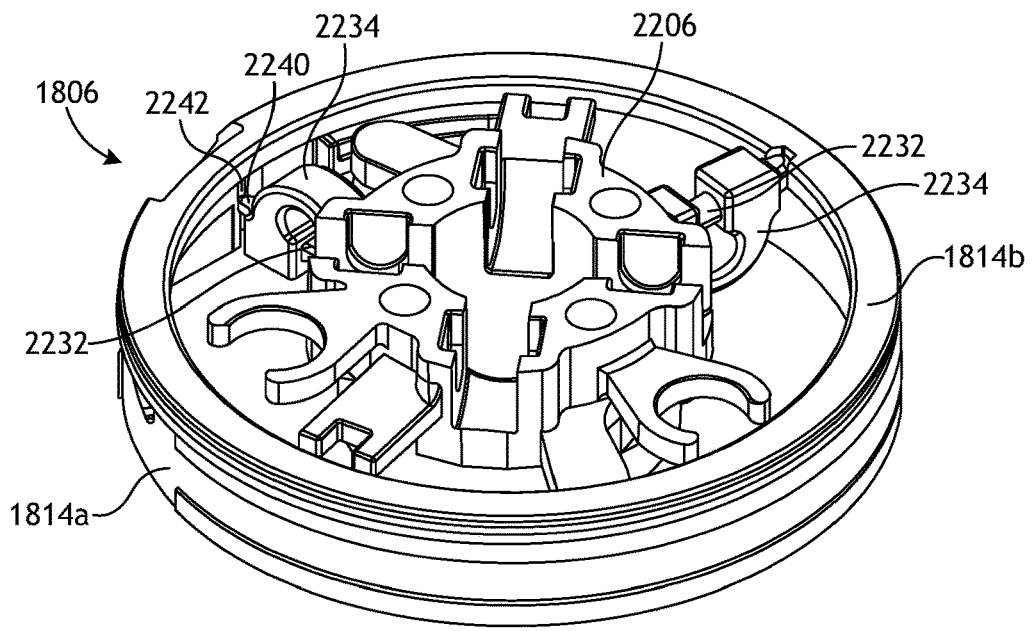
FIG. 22G is an isometric view of a portion of the slipper clutch mechanism of FIG. 22E, according to one or more embodiments.

FIG. 22G is an isometric view of a portion of the slipper clutch mechanism 1806, according to one or more embodiments. In the illustrated embodiment, the column 2206 provides at least two guide bars 2232 extending laterally from the column 2206, and corresponding compliant members 2234 rest on the respective guide bars 2232. One compliant member 2234 extends to contact the dwell ring 1814b, as described above, while the other compliant member 2234 may extend to contact the bailout starter ring 1814a. More specifically, the projection 2240 of the compliant member 2234 contacting the bailout starter ring 1814a may be received within a detent 2242 defined in the bailout starter ring 1814, which ensures that the bailout starter ring 1814a stays stationary until the slipper clutch mechanism 1806 is actuated. Upon rotating the slip carrier 1812 (FIG. 22F), as generally described herein, the compliant member 2234 may flex and allow the projection 2240 to be urged out of the detent 2242 as the bailout starter ring 1814a begins to rotate. In some cases, this may provide tactile feedback to the user.

Figure 22H:
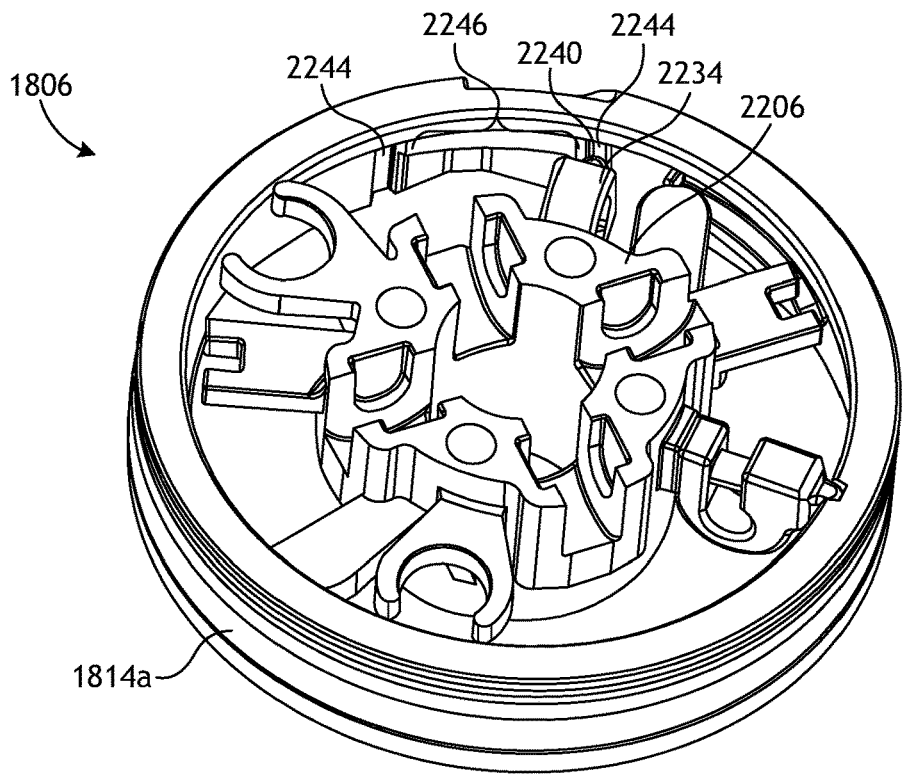
FIG. 22H is another isometric view of a portion of the slipper clutch mechanism of FIG. 22E, according to one or more embodiments.

FIG. 22H is another isometric view of a portion of the slipper clutch mechanism 1806, according to one or more embodiments. In some embodiments, as illustrated, the inner surface of the bailout starter ring 1814a may define or otherwise provide two or more detents 2244 (two shown). In such embodiments, the projection 2240 of the compliant member 2234 contacting the bailout starter ring 1814a may be configured to be locate and received within each detent 2244 upon rotating the bailout starter ring 1814a. The first detent 2244 may be configured to ensure that the bailout starter ring 1814a is prevented from rotating until the user activates it (prevents unintended activation, movement due to transportation, etc.). The second detent 2244 may maintain the position of the bailout starter ring 1814a after the pin 1820 (FIGS. 20 and 21A-21C) has exited the first interface 2010a (FIGS. 20 and 21A). This may ensure the latch defeat and decoupling actuations are maintained after exit. This may also aide with reversing the bailout, if necessary.

Moreover, in some embodiments, the inner surface of the bailout starter ring 1814a may vary radially across a portion 2246 (or entirely) to alter the deformation of the compliant member 2234 as the bailout starter ring 1814a rotates relative to the column 2206. The result is varying drag on the bailout starter ring 1814a that is dependent upon the angular orientation of the bailout starter ring 1814a. One advantage to the variable surface of the portion 2246 is to compensate for varying actuation torque due to the loading/unloading of springs and ramps (e.g., latch defeat, decoupling, etc.). The varying inner surface of the portion 2246 may begin with a relatively low inner radius while the spring deformation in the latch lock defeat, for example, is low. Then, the inner radius of the portion 2246 may increase to reduce force as the bailout starter ring 1814a turns so the load felt by the user is constant. In addition, the inner radius of the portion 2246 may undulate or may be "wavy" to provide rumble strips or the like for increased tactile feedback.

Mule Bailout—Single Direction Bailout Ring

Figure 23A:
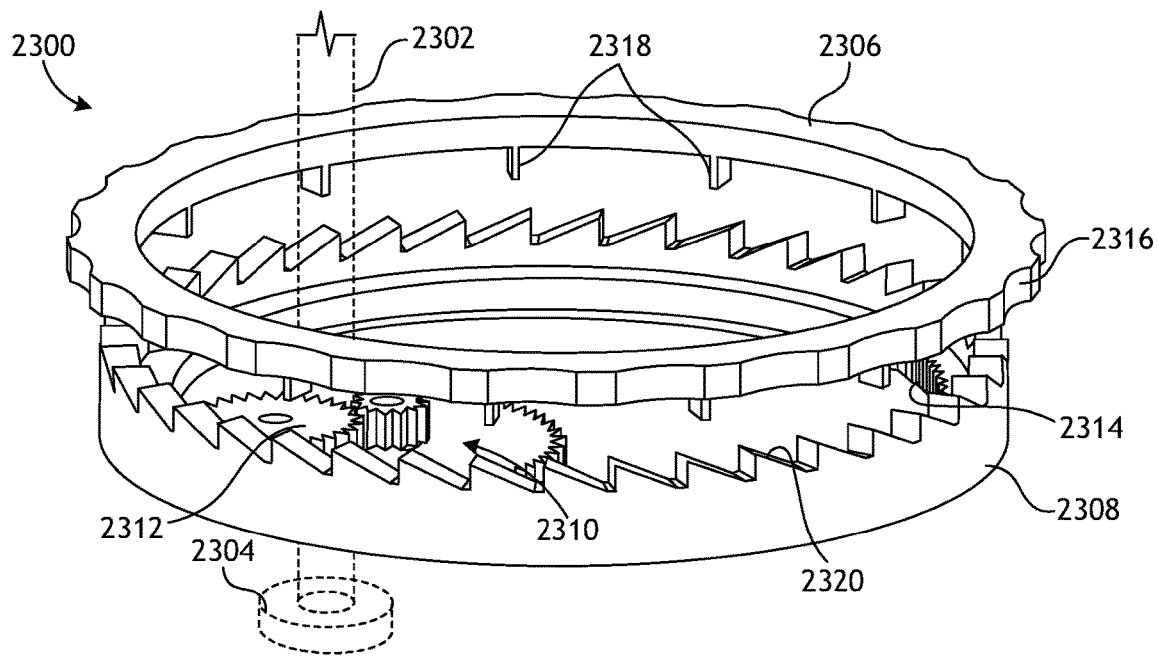
FIGS. 23A and 23B are isometric views of an example slipper clutch bailout mechanism, according to one or more embodiments.
Figure 23B:
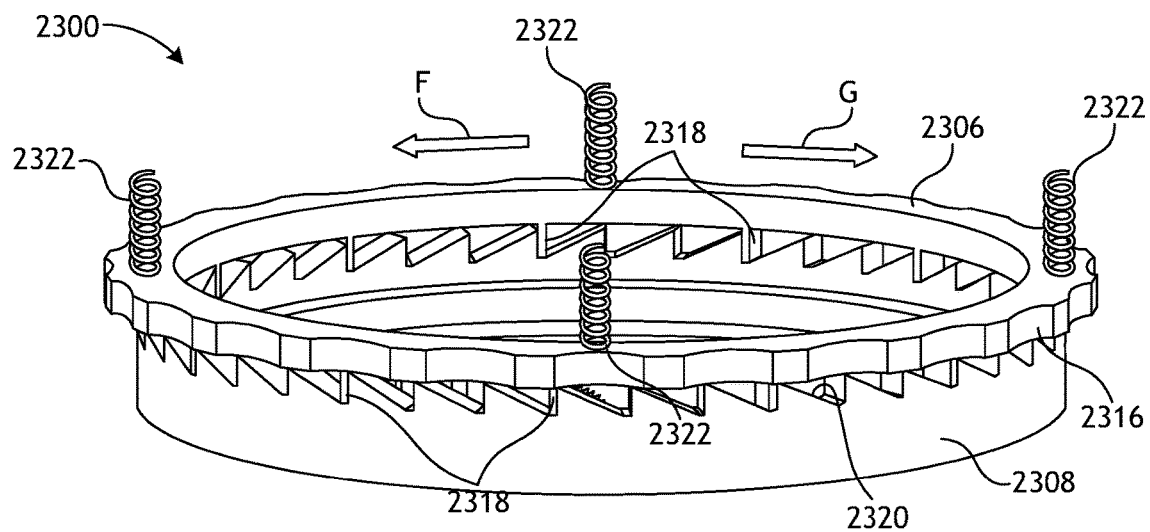

FIGS. 23A and 23B are isometric views of an example slipper clutch bailout mechanism 2300, according to one or more embodiments. The slipper clutch bailout mechanism 2300 may be similar in some respects to the slipper clutch bailout mechanism 1806 of FIGS. 18-21C. In some embodiments, the slipper clutch bailout mechanism 2300 may replace the slipper clutch bailout mechanism 1806 in the handle 1618a (FIG. 18) to accomplish the same or different tool bailout needs of the surgical tool 1600 (FIGS. 16-17B).

Referring first to FIG. 23A, in the illustrated embodiment, the slipper clutch mechanism 2300 may be manually actuatable to drive a spline 2303 (shown in dashed lines) extending from or otherwise operatively coupled to a drive input 2304 (shown in dashed lines). The spline 2303 may be the same as or similar to either of the splines 1624a,c of FIG. 18, and the drive input 2304 may be the same as or similar to either of the drive inputs 1624a,c of FIG. 18. Accordingly, actuation of the drive input 2304 may cause the spline 2303 to rotate and correspondingly translates (e.g., retracts) a knife at the end effector 1604 (FIGS. 16 and 17B) or open/close the jaws 1610, 1612 (FIGS. 16 and 17B) of the end effector 1604. In other embodiments, actuation of the drive input 2304 can cause other tool functions, such as articulation of the end effector 1604 at the wrist 1606 (FIG. 16) or translating the shaft 1602 (FIGS.>16 and 17A-17B).

As illustrated, the slipper clutch bailout mechanism 2300 may include a bailout ring 2306 and a ring gear 2308 axially offset from the bailout ring 2306. The ring gear 2308 may be operatively coupled to the spline 2303 via a drive mechanism 2310 such that manual actuation (rotation) of the ring gear 2308 may correspondingly rotate the spline 2303. The drive mechanism 2310 may include any of a variety of interconnected gears, belts, chains, sprockets, etc. configured to ultimately drive the spline 2303. In the illustrated embodiment, the drive mechanism 2310 comprises a type of gear train that includes a plurality of interconnected (or intermeshed) gears configured to ultimately intermesh with and drive the spline 2303. The gear train, for example, may include a pinion gear 2312 arranged to intermesh with inner radial teeth 2314 defined on an inner radial surface of the ring gear 2308, and the pinion gear 2312 may be operatively coupled to and otherwise intermesh with one or more other gears included in the gear train such that rotating the ring gear 2308 causes the drive mechanism 2310 to drive the spline 2303 in rotation.

While only one drive mechanism 2310 is depicted in FIG. 23A, it will be appreciated that more than one drive mechanism 2310 may be employed in the slipper clutch bailout mechanism 2300. More specifically, it is contemplated herein that actuation of the slipper clutch mechanism 2300 may cause bailout of a plurality of functions or operations of the surgical tool 1600 (FIG. 16), either sequentially or simultaneously. Consequently, the combination of the bailout ring 2306 and the ring gear 2308 may be capable of bailing out multiple functions/operations, without departing from the scope of the disclosure.

In the illustrated embodiment, the bailout ring 2306 may provide or otherwise define a gripping interface 2316 configured to be gripped or grasped by a user to manually manipulate the bailout ring 2306. In the illustrated embodiment, the gripping interface 2316 comprises a series of alternating indentations and projections defined on the outer circumference of the bailout ring, but could alternatively comprise any other type of feature or structure engageable or graspable by a user's hand.

The bailout ring 2306 may further define or otherwise provide one or more engagement features 2318 extending distally from the bailout ring 2306 and engageable with ratchet teeth 2320 defined on the ring gear 2308. In the illustrated embodiment, each engagement feature 2318 comprises a generally planar or flat tab, but could alternately comprise any structure or feature configured to mate with the ratchet teeth 2320 as described below.

In FIG. 23B, the bailout ring 2306 has been moved to engage the ring gear 2308. More specifically, a user may manually grasp the bailout ring 2306 at the gripping interface 2316 and move the bailout ring 2306 axially along the tool axis until the engagement features 2318 provided by the bailout ring 2306 properly mate with the ratchet teeth 2320 provided by the ring gear 2308. In at least one embodiment, the slipper clutch mechanism 2300 may include one or more guide features (not shown) that help guide the bailout ring 2306 axially and into engagement with the ring gear 2308. Such guide features can include, for example, a plurality of rails extending between the bailout ring 2306 and the ring gear 2308, but other types of guide structures could be employed, without departing from the scope of the disclosure.

With the engagement features 2318 engaged with the ratchet teeth 2320, the user may manually rotate the bailout ring 2306 in a first angular direction (e.g., counter-clockwise), as indicated by the arrow F. As the bailout ring 2306 rotates in the first angular direction F, the ring gear 2308 will correspondingly rotate in the same direction F via the engagement between the engagement features 2318 and the ratchet teeth 2320. Moreover, rotating the ring gear 2308 in the first angular direction F may cause actuation of the drive mechanism 2310 (FIG. 23A), and thereby rotate the spline 2303 (FIG. 23A) and bailout one or more functions or configurations of the surgical tool 1600 (FIG. 16). In contrast, if the user rotates the bailout ring 2306 in a second direction (e.g., clockwise), as indicated by the arrow G, the engagement features 2318 will ratchet over the angled ratchet teeth 2320, thus not driving the ring gear 2308 in the direction G.

In some embodiments, the slipper clutch mechanism 2300 may further provide or include one or more springs 2322 arranged to provide a downward force on the bailout ring 2306 to help with engagement with the ring gear 2308. More particularly, the springs 2322 may help to keep the engagement features 2318 engaged with the ratchet teeth 2320, which may be especially advantageous when the bailout ring 2306 is rotated in the second angular direction G.

Open/Close Knob with Internal Crown Internal Combo Ring

Figure 24:
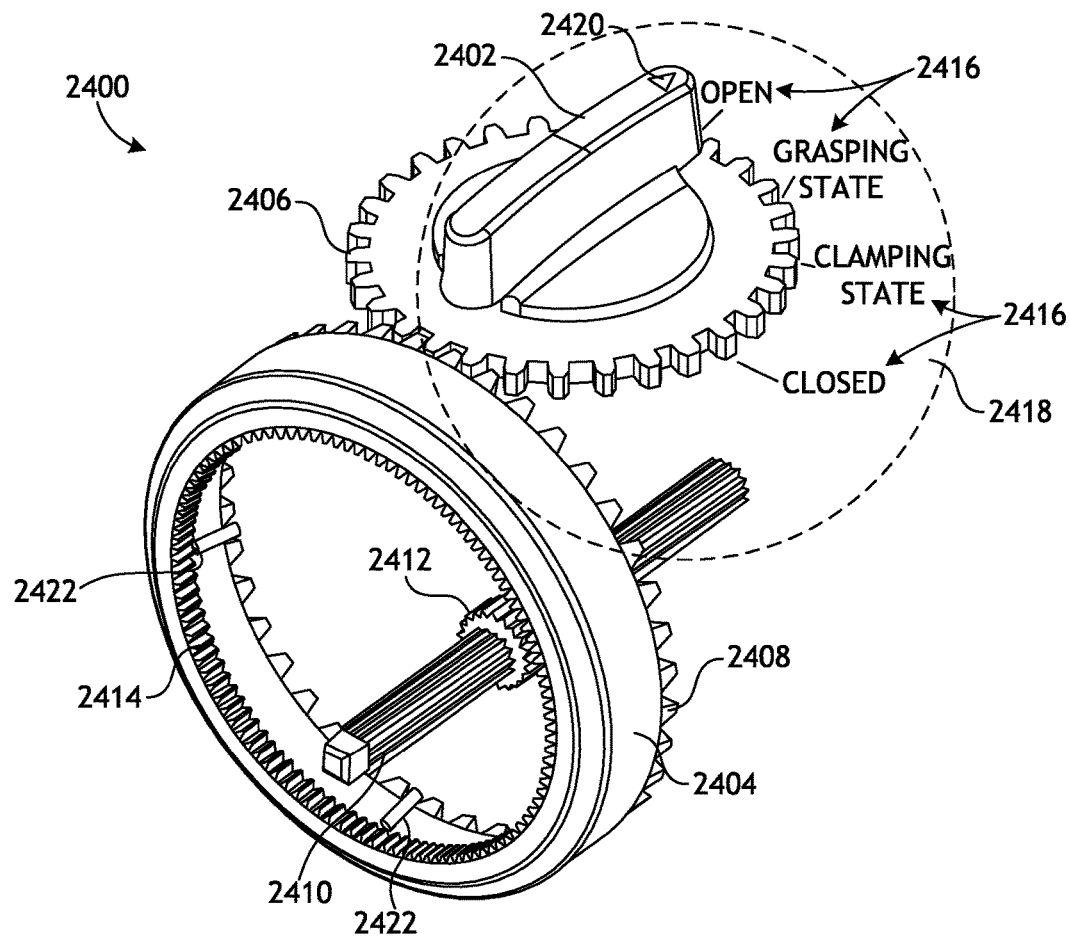
FIG. 24 is an isometric view of an example bailout device, according to one or more embodiments.

FIG. 24 is an isometric view of an example bailout device 2400, according to one or more embodiments. The bailout device 2400 may be similar in some respects to the bailout device 1822 of FIG. 18 and, therefore, may be designed to manually bail out one or more functions or configurations of the surgical tool 1600 (FIG. 16), such as manually opening or closing the jaws 1610, 1612 (FIGS. 16 and 17B) of the end effector 1604 (FIGS. 16 and 17B). In some embodiments, the bailout device 2400 may be used in conjunction with the slipper clutch mechanism 1806 of FIGS. 18-21C and may replace the bailout device 1822. In other embodiments, however, the bailout device 2400 may entirely replace the slipper clutch mechanism 1806. In such embodiments, the bailout device 2400 may be coupled to the handle 1618a (FIGS. 16 and 18) and may otherwise be installed by itself in the surgical tool 1600, without departing from the scope of the disclosure.

As illustrated, the bailout device 2400 may include a knob 2402 engageable with a crown gear 2404. The knob 2402 may be rotatably mounted to the outer housing 2418 of the handle 1618a (FIGS. 16 and 18) and may provide or otherwise define a drive gear 2406 arranged to engage or intermesh with corresponding gear teeth 2408 defined on the crown gear 2404. In such embodiments, the drive gear 2406 may form an integral part of the knob 2402 such that manually turning (rotating) the knob 2402 will correspondingly rotate the drive gear 2406 and drive the crown gear 2404 in rotation.

The crown gear 2404 may be operatively coupled to a spline 2410, which may be the same as or similar to either of the splines 1624a,c of FIG. 18. Consequently, rotating the spline 2410 may correspondingly translate (e.g., retract) a knife at the end effector 1604 (FIGS. 16 and 17B) or open/close the jaws 1610, 1612 (FIGS. 16 and 17B) of the end effector 1604. In other embodiments, however, rotation of the spline 2410 may cause other tool functions, such as articulation of the end effector 1604 at the wrist 1606 (FIG. 16).

In the illustrated embodiment, a pinion gear 2412 may be coupled to the spline 2410 and engageable with radial gear teeth 2414 defined by the crown gear 2404 such that movement (rotation) of the crown gear 2404 correspondingly drives the pinion gear 2412 and rotates the spline 2410. Accordingly, rotating the crown gear 2404 via manual rotation (actuation) of the knob 2402 may cause the spline 2410 to rotate. In some embodiments, the gear ratio between the drive gear 2406 and the gear teeth 2408 defined on the crown gear 2404 and/or the gear ratio between the pinion gear 2412 and the radial gear teeth 2414 of the crown gear 2404 may be adjusted such that the bailout function can be accomplished by rotating the knob 2402 less than 360° and, preferably, less than 180°.

In some embodiments, the bailout device 2400 may be configured to manually open or close the jaws 1610, 1612 (FIGS. 16 and 17B) of the end effector 1604 (FIGS. 16 and 17B), as indicated above. In such embodiments, various markings 2416 may be included on the housing 2418. The markings 2416 may include a label, a decal, a graphic, or any other visual indicator that may be provided on the housing 2418. Example markings 2416 include textual statements/conditions of the position of the jaws 1610, 1612 such as, but not limited to, OPEN, GRASPING STATE, CLAMPING STATE, and CLOSED. The knob 2402 may be manually rotated to any of the foregoing markings 2416, and via the interaction between the crown gear 2404, the pinion gear 2412, and the spline 2410, the jaws 1610, 1612 may be configured to transition to the indicated state/condition at the end effector 1604. In at least one embodiment, the knob 2402 may include or provide a corresponding marking 2420, such as an arrowhead, that may be aligned with the markings 2416 provided on the housing 2418.

In some embodiments, the bailout device 2400 may include one or more bearings used to help support movement and operation of the various component parts thereof. In one or more embodiments, for example, the bailout device 2400 may include a plurality of roller bearings 2422 (two shown) arranged on an inner circumference 2424 of the crown gear 2404 to support the crown gear 2402 during operation from radial loading. In at least one embodiment, one or more additional roller bearings (not shown) may be arranged at or near the interior engagement between the drive gear 2406 and the gear teeth 2408 defined on the crown gear 2404. Such roller bearings may help support the crown gear 2404 from thrust forces attributable to manual actuation of the knob 2402.

Combined Knife Retraction and Jaw Release Bailout

Figure 25:
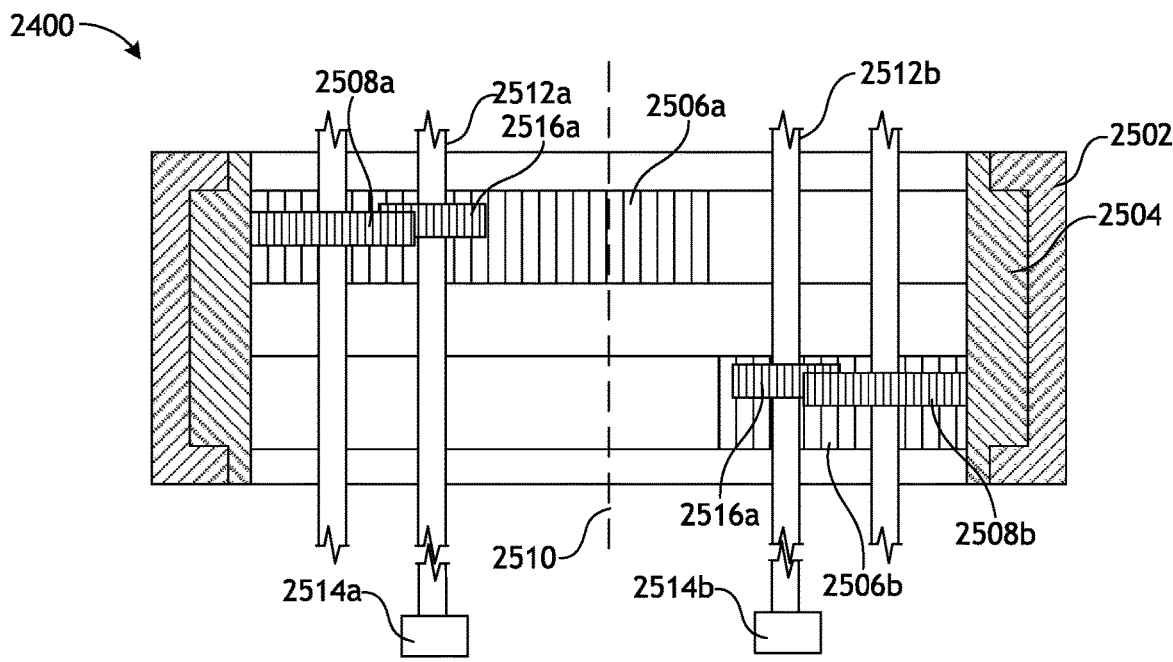
FIG. 25 is a cross-sectional side view of an example bailout system, according to one or more embodiments.

FIG. 25 is a cross-sectional side view of an example bailout system 2500, according to one or more embodiments. The bailout system 2500 may be similar in some respects to the slipper clutch mechanism 1806 of FIGS. 18-21C and, therefore, may be designed to manually bail out one or more functions or configurations of the surgical tool 1600 (FIG. 16), such as manually opening or closing the jaws 1610, 1612 (FIGS. 16 and 17B) of the end effector 1604 (FIGS. 16 and 17B), and/or manually translating (e.g., retracting) a knife at the end effector 1604 (FIGS. 16 and 17B). In some embodiments, the bailout system 2500 may be arranged at the handle 1618a (FIGS. 16 and 18), but could alternatively be arranged at any other location on the surgical tool 1600, without departing from the scope of the disclosure.

As illustrated, the bailout system 2500 may include a cover 2502 and a bailout ring 2504 arranged radially inward from the cover 2502. The cover 2502 may be movable or removable in order to expose the bailout ring 2504. In some embodiments, the bailout ring 2504 may be configured to be manually grasped or gripped by a user and rotated to manually bail out the surgical tool 1600 (FIG. 16) when needed. In the illustrated embodiment, the bailout ring 2504 may provide or otherwise define a first series of inner gear teeth 2506a and a second series of inner gear teeth 2506b. A first drive gear 2508a may be arranged to intermesh with the first series of inner gear teeth 2506a such that rotation of the bailout ring 2504 about a tool axis 2508 will correspondingly rotate the first drive gear 2508a. Similarly, a second drive gear 2508b may be arranged to intermesh with the second series of inner gear teeth 2506b such that rotation of the bailout ring 2504 about the tool axis 2510 will correspondingly rotate the first drive gear 2508a.

In the illustrated embodiment, a first spline 2512a is operatively coupled to or otherwise extends from a first drive input 2514a, and a second spline 2512b is operatively coupled to or otherwise extends from a second drive input 2514b. The splines 2512a,b may be the same as or similar to the splines 1624a,c of FIG. 18, and the drive inputs 2514a,b may be the same as or similar to the drive inputs 1636b,d of FIG. 18. Accordingly, actuation of the first drive input 2514a may cause the first spline 2512a to rotate and correspondingly translate (e.g., retract) a knife at the end effector 1604 (FIGS. 16 and 17B), and actuation of the second drive input 2514b may cause the second spline 2512b to rotate and correspondingly open/close the jaws 1610, 1612 (FIGS. 16 and 17B) of the end effector 1604. In other embodiments, actuation of one of the drive inputs 2514a,b may cause other tool bailout functions, such as articulation of the end effector 1604 at the wrist 1606 (FIG. 16).

As illustrated a first pinion gear 2516a may be coupled to the first spline 2512a and arranged to intermesh with the first drive gear 2508a, and a second pinion gear 2516b may be coupled to the second spline 2512b and arranged to intermesh with the second drive gear 2508b. Consequently, as the bailout ring 2504 is manually actuated (rotated), the first drive gear 2508a may drive the first pinion gear 2516a, which causes the first spline 2512a to rotate and thereby manually translate (e.g., retract) a knife at the end effector 1604 (FIGS. 16 and 17B). Similarly, as the bailout ring 2504 is manually actuated (rotated), the second drive gear 2508b may drive the second pinion gear 2516b, which causes the second spline 2512a to rotate and thereby manually open/close the jaws 1610, 1612 (FIGS. 16 and 17B) of the end effector 1604. Accordingly, the bailout system 2500 may allow continuous knife translation (e.g., retraction) and jaw release via direct drive of the firing and closure splines 2512a,b with a single user input at the bailout ring 2504.

In some embodiments, the bailout ring 2504 is in constant interaction with the pinion gears 2516a,b on the splines 2512a,b, respectively. During normal operation of the surgical tool 1600 (FIG. 16), the bailout ring 2504 may be engaged with the first pinion gear 2516a and the first spline 2512a (i.e., the knife firing system) via the first series of inner gear teeth 2506a and may rotate during knife firing and retraction. During a bailout situation, however, the user may grasp and turn the bailout ring 2504, which causes the knife to translate (e.g., retract). Moreover, the first and second series of inner gear teeth 2506a,b may be configured such that at the end of knife retraction, the second series of inner gear teeth 2506b will engage the second drive gear 2508b and thereby drive the second pinion gear 2516a to rotate the second spline 2512b, which causes the jaws 1610, 1612 (FIGS. 16 and 17B) to open. In at least one embodiment, the user must manually rotate the bailout ring 2504 one full revolution to both retract the knife and open the jaws 1610, 1612, but could alternatively be required to rotate the bailout ring 2504 more or less than a full revolution to retract the knife and open the jaws 1610, 1612, without departing from the scope of the disclosure.

Figure 26A:
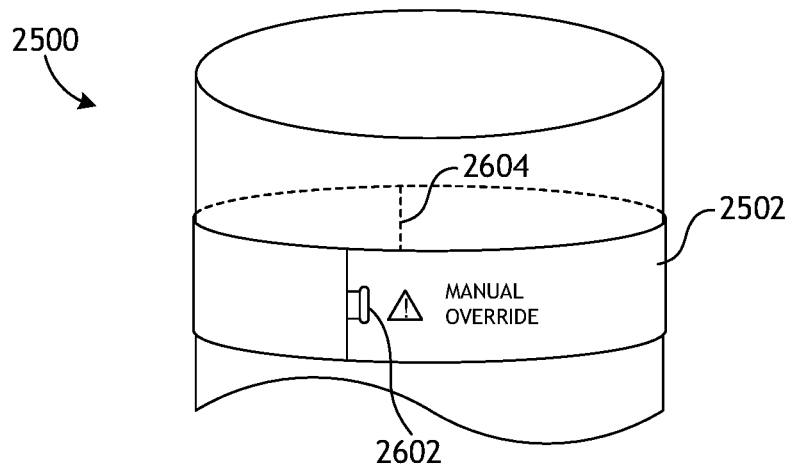
FIGS. 26A-26C are schematic side views of various examples of the bailout system of FIG. 25, according to one or more embodiments.
Figure 26B:
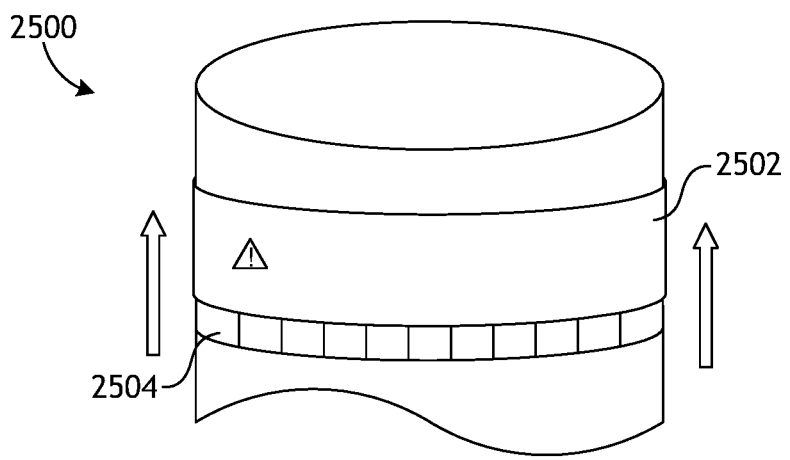
Figure 26C:
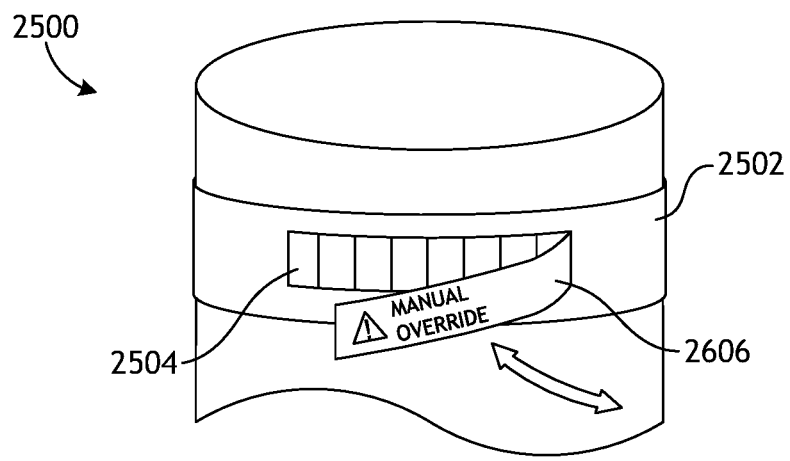

FIGS. 26A-26C are schematic side views of various examples of the bailout system 2500 of FIG. 25, according to one or more embodiments. In some embodiments, as illustrated, the cover 2502 may be configured to occlude the bailout ring 2504 to prevent a user from inadvertently activating (actuating) the bailout system 2500. When is it desired to actuate the bailout system 2500, the cover 2502 must be moved or removed to expose the bailout ring 2504 and enable the user to manually grasp or otherwise manipulate (e.g., rotate) the bailout ring 2504.

In FIG. 26A, for example, the cover 2502 comprises a removable clamshell that includes a latch 2602 and a hinge 2604. The cover 2502 can be opened to expose the bailout ring 2504 by releasing the latch 2602 and pivoting the clamshell halves open at the hinge 2604. In FIG. 26B, the cover 2502 may be moved axially (either proximally or distally) to expose the bailout ring 2504. In such embodiments, the cover 2502 may be spring-loaded to return the cover 2502 back to its natural position once the user disengages the cover 2502. In FIG. 26C, the cover 2502 may include a hinged bailout door 2606 pivotably attached to the cover 2502. The bailout door 2606 may be opened and catch on external gear teeth of the bailout ring 2504. Consequently, the bailout door 26060 may be pivoted back and forth to ratchet against the external gear teeth of the bailout ring 2504 to rotate and advance the bailout ring 2504.

Figure 27A:
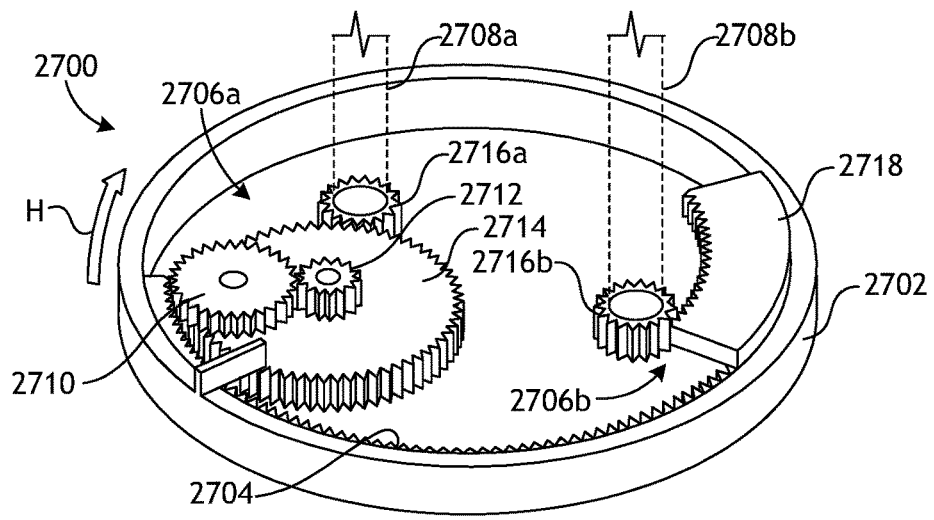
FIGS. 27A-27C are isometric views of another example bailout system, according to one or more embodiments.
Figure 27B:
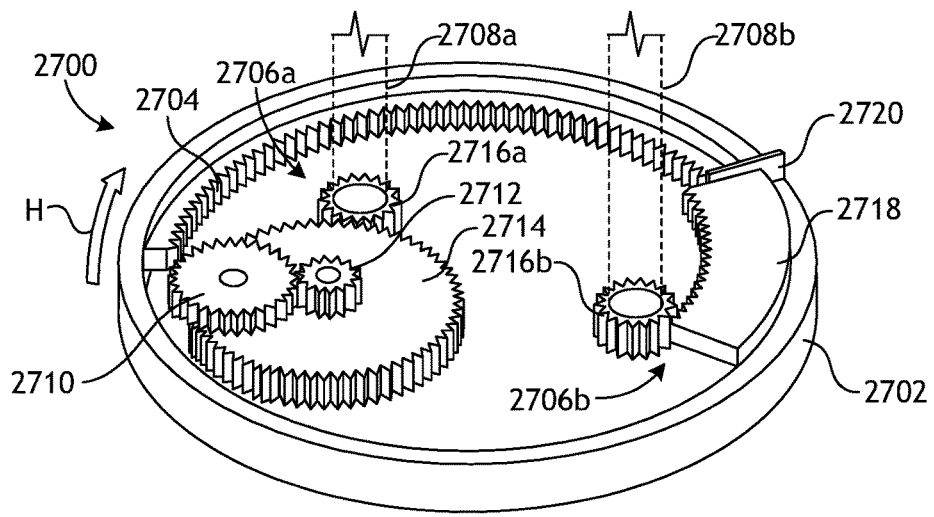
Figure 27C:
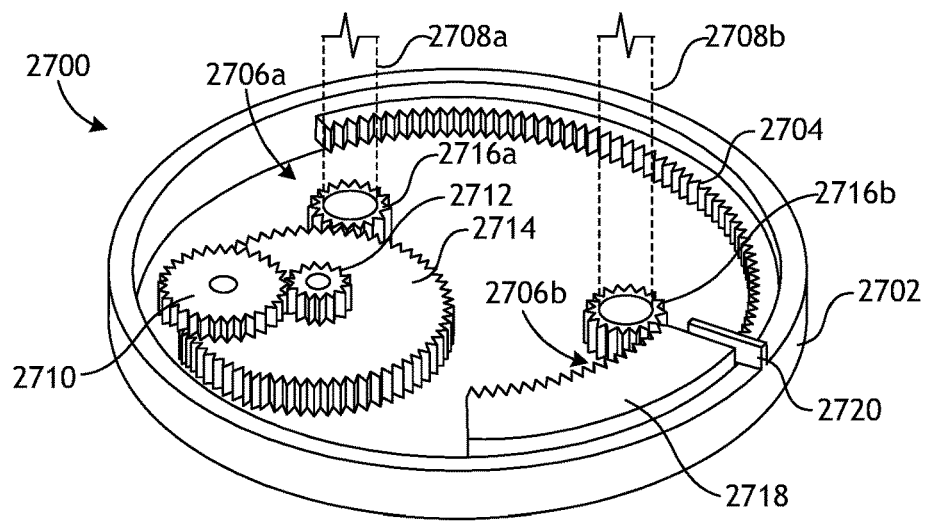

FIGS. 27A-27C are isometric views of another example bailout system 2700, according to one or more embodiments. The bailout system 2700 may be similar in some respects to the bailout system 2500 of FIG. 25 and, therefore, may be operable to allow a user to manually bail out one or more functions or configurations of the surgical tool 1600 (FIG. 16), such as manually opening or closing the jaws 1610, 1612 (FIGS. 16 and 17B) of the end effector 1604 (FIGS. 16 and 17B), and/or manually translating (e.g., retracting) a knife at the end effector 1604 (FIGS. 16 and 17B). In some embodiments, the bailout system 2700 may be arranged at the handle 1618a (FIGS. 16 and 18), but could alternatively be arranged at any other location on the surgical tool 1600, without departing from the scope of the disclosure.

As illustrated, the bailout system 2700 may include a bailout ring 2702 that may be manually grasped or otherwise manipulated by a user to commence the bailout process. The bailout ring 2702 may provide or otherwise define a series of inner gear teeth 2704 engageable with a first drive mechanism 2706a, which may include any of a variety of interconnected gears, belts, chains, sprockets, etc. configured to ultimately drive a first spline 2708a. In the illustrated embodiment, the first drive mechanism 2706a comprises a type of gear train that includes a plurality of interconnected (or intermeshed) gears configured to ultimately drive the first spline 2708a by rotating the bailout ring 2702. The gear train, for example, may include a first drive gear 2710 arranged to intermesh with the inner gear teeth 2704, a sprocket 2712 that intermeshes with the first drive gear 2710, a second drive gear 2714 attached to the sprocket 2712 such that rotation of the sprocket 2712 rotates the second drive gear 2714, and a first pinion gear 2716a coupled to the first spline 2708a and arranged to intermesh with the second drive gear 2714. Accordingly, manual actuation (rotation) of the bailout ring 2702 may cause the first spline 2708a to correspondingly rotate via the interconnected gearing of the first drive mechanism 2706a.

The bailout system 2700 may also include a second drive mechanism 2706b that may include any of a variety of interconnected gears, belts, chains, sprockets, etc. configured to ultimately drive a second spline 2708b. In the illustrated embodiment, the second drive mechanism 2706b comprises a sector gear 2718 arranged to intermesh with a second pinion gear 2716b coupled to the second spline 2708b. Accordingly, actuation (rotation) of the second drive mechanism 2706b may cause the second spline 2708b to correspondingly rotate.

The splines 2708a,b may be the same as or similar to the splines 1624a,c of FIG. 18. Accordingly, rotation of the first spline 2708a may correspondingly translate (e.g., retract) a knife at the end effector 1604 (FIGS. 16 and 17B), and rotation of the second spline 2708b may correspondingly open/close the jaws 1610, 1612 (FIGS. 16 and 17B) of the end effector 1604, or vice versa. In other embodiments, rotation of one of the splines 2708a,b may alternately cause other tool bailout functions, such as articulation of the end effector 1604 at the wrist 1606 (FIG. 16).

Example operation of the bailout system 2700 is now provided. In FIG. 27A, the bailout ring 2702 may be manually rotated about a tool axis, as indicated by the arrow H. As the bailout ring 2702 rotates, the inner gear teeth 2704 engage and drive the first drive mechanism 2706a (e.g., the first drive gear 2710), which correspondingly drives the first pinion gear 2716a. Rotating the first pinion gear 2716a causes the first spline 2708a to rotate and thereby manually translate (e.g., retract) a knife at the end effector 1604 (FIGS. 16 and 17B).

In FIG. 27B, the bailout ring 2702 is manually rotated further in the direction H until a stop member 2720 attached to the bailout ring 2702 engages a lateral end of the sector gear 2718. At this point the inner gear teeth 2704 of the bailout ring 2702 may have rotated past the first drive mechanism 2706b and thereby cease to actuate the first drive mechanism 2706b.

In FIG. 27C, further rotation of the bailout ring 2702 in the direction H may actuate the second drive mechanism 2706b. More specifically, further rotation of the bailout ring 2702 pushes the stop member 2720 against the sector gear 2718 and thereby causes the sector gear 2718 to rotate in the same direction to drive the second pinion gear 2716b. Rotating the second pinion gear 2716b correspondingly causes the second spline 2708a to rotate and thereby manually open/close the jaws 1610, 1612 (FIGS. 16 and 17B) of the end effector 1604.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes or functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
a handle having a drive input and a spline operatively coupled to the drive input, wherein rotating the spline causes operation of a function of the robotic surgical tool;
a bailout ring arranged at the handle;
a slipper clutch mechanism received within the bailout ring and including:
a slip carrier rotationally fixed to the bailout ring and defining a vertical slot that slidably receives a pin;
a first ring arranged within the slip carrier and defining a first interface;
a second ring arranged within the slip carrier atop the first ring and defining a second interface; and
a pinion gear operatively coupled to the spline and arranged to intermesh with radial gear teeth defined on the second ring,
wherein manual rotation of the bailout ring rotates the slip carrier and the pin in the same direction and thereby rotates the first ring when the pin is received within the first interface,
wherein manual rotation of the bailout ring rotates the second ring once the pin locates and is received within the second interface, and
wherein rotating the second ring drives the pinion gear and rotates the spline to manually bail out the function of the robotic surgical tool.

2. The robotic surgical tool of claim 1, further comprising:
a drive housing that includes the handle at a first end and has a lead screw extending from the handle;
a carriage movably mounted to the lead screw such that rotation of the lead screw from the handle causes the carriage to move axially along the lead screw; and
an elongate shaft extending from the carriage and penetrating the handle, the shaft having an end effector arranged at a distal end thereof,
wherein the function of the robotic surgical tool is selected from the group consisting of translating a knife at the end effector, opening or closing opposing jaws of the end effector, articulating an orientation of the end effector at a wrist interposing the shaft and the end effector, retracting a biopsy needle, disconnecting electrocautery, opening scissors, releasing a clip, translation of the handle, decoupling, and locking of an insertion drive.

3. The robotic surgical tool of claim 1, wherein the drive input is a first drive input, the spline is a first spline, the function is a first function, and the pinion gear is a first pinion gear, the robotic surgical tool further comprising a second drive input arranged at the handle and a second spline operatively coupled to the second drive input and rotatable to cause operation of a second function of the robotic surgical tool, and wherein the slipper clutch mechanism further includes:
a crown gear arranged atop the second ring;
a bailout device including a knob and a drive gear engageable with gear teeth defined on the crown gear; and
a second pinion gear operatively coupled to the second spline and arranged to intermesh with radial gear teeth defined on the crown gear,
wherein manual rotation of the knob rotates the crown gear and thereby rotates the second spline to manually bail out the second function of the robotic surgical tool.

4. The robotic surgical tool of claim 3, further comprising one or more markings provided on a housing of the handle and indicating a corresponding one or more conditions of the function of the robotic surgical tool, wherein rotating the knob to align with the a given marking of the one or more markings will transition the function of the robotic surgical tool to a condition of one or more conditions corresponding to the given marking.

5. The robotic surgical tool of claim 1, wherein the slipper clutch mechanism further includes a third ring interposing the first and second rings and defining a third interface, the third ring being rotatable relative to the first and third rings, and wherein manual rotation of the bailout ring rotates the third ring once the pin locates and is received within the third interface.

6. The robotic surgical tool of claim 1, wherein the spline is operatively coupled to the drive input via a drive shaft extending from the drive input, and wherein the slipper clutch mechanism further includes a decoupling mechanism that comprises:
a ramp defined on an inner surface of the first ring; and
a decoupling plunger cap mounted to the drive shaft and providing a radial flange engageable with the ramp,
wherein rotating the first ring moves the ramp into engagement with the radial flange and thereby moves the decoupling plunger cap relative to drive shaft to decouple the drive input from a drive output of an instrument driver.

7. The robotic surgical tool of claim 1, wherein the slipper clutch mechanism further includes an anti-reverse mechanism that includes a spring-actuated pawl engageable with ratchet teeth defined on an inner surface of the slip carrier, wherein the pawl allows the slip carrier to rotate in a first direction, but engages the ratchet teeth to prevent the slip carrier from rotating in a second direction opposite the first direction.

8. The robotic surgical tool of claim 7, wherein operation of the anti-reverse mechanism provides audible or tactile feedback to a user.

9. The robotic surgical tool of claim 1, wherein the slipper clutch mechanism further includes a latch lock defeat mechanism that includes:
a column;
a lifter having a foot received within a pocket defined in the column, a lifter shaft extending from the foot, and a locking tab arranged in the pocket that prevents the foot from exiting the pocket; and
a ramp defined on the first ring and engageable with a lateral tab provided on the lifter shaft,
wherein rotating the first ring moves the ramp into engagement with the lateral tab and moves the lifter proximally to transition the locking tab from a latched position, where the locking tab extends out of the pocket and inhibits unlatching of the handle from an instrument driver, and a released position, where the locking tab is stowed within the pocket and allows a latch ring to move and detach the handle from the instrument driver.

10. A method of operating a robotic surgical tool, comprising:
arranging the robotic surgical tool adjacent a patient, the robotic surgical tool including a handle having a first drive input and a first spline operatively coupled to the first drive input and rotatable to operate a first function of the robotic surgical tool, a bailout ring arranged at the handle, and a slipper clutch mechanism received within the bailout ring, the slipper clutch mechanism including:

a slip carrier rotationally fixed to the bailout ring and defining a vertical slot that slidably receives a pin;
a first ring arranged within the slip carrier and defining a first interface;
a second ring arranged within the slip carrier atop the first ring and defining a second interface; and
a first pinion gear operatively coupled to the spline and arranged to intermesh with radial gear teeth defined on the second ring;
manually rotating the bailout ring and thereby rotating the slip carrier and the pin in the same direction;
rotating the first ring with the pin received within the first interface;
locating and entering the second interface with the pin as the first ring rotates;
rotating the second ring with the pin received within the second interface; and
driving the first pinion gear and the second spline with the second ring and thereby manually bailing out the first function of the robotic surgical tool.

11. The method of claim 10, wherein the robotic surgical tool further includes a drive housing that includes the handle at a first end and has a lead screw extending from the handle, a carriage movably mounted to the lead screw such that rotation of the lead screw from the handle causes the carriage to move axially along the lead screw, and an elongate shaft extending from the carriage and penetrating the handle, the shaft having an end effector arranged at a distal end thereof, and
wherein the function of the robotic surgical tool is selected from the group consisting of translating a knife at the end effector; opening or closing opposing jaws of the end effector, and articulating an orientation of the end effector at a wrist interposing the shaft and the end effector, retracting a biopsy needle, disconnecting electrocautery, opening scissors, releasing a clip, translation of the handle, decoupling, and locking of an insertion drive.

12. The method of claim 10, wherein the robotic surgical tool further includes a second drive input arranged at the handle and a second spline operatively coupled to the second drive input and rotatable operate a second function of the robotic surgical tool, the slipper clutch mechanism further including:
a crown gear arranged atop the second ring;
a bailout device including a knob and a drive gear engageable with gear teeth defined on the crown gear; and
a second pinion gear operatively coupled to the second spline and arranged to intermesh with radial gear teeth defined on the crown gear, the method further comprising:
manually rotating the knob and thereby rotating the crown gear; and
driving the second pinion gear and the second spline with the crown gear and thereby manually bailing out the second function of the robotic surgical tool.

13. The method of claim 10, wherein the slipper clutch mechanism further includes a third ring interposing the first and second rings and defining a third interface, the method further comprising:
locating and entering the third interface with the pin; and
rotating the third ring with the pin received within the third interface.

14. The method of claim 10, wherein the spline is operatively coupled to the drive input via a drive shaft extending from the drive input, and wherein the slipper clutch mechanism further includes a decoupling mechanism that comprises:
a ramp defined on an inner surface of the first ring; and
a decoupling plunger cap mounted to the drive shaft and providing a radial flange engageable with the ramp, wherein rotating the first ring comprises:
moving the ramp into engagement with the radial flange;
moving the decoupling plunger cap relative to drive shaft with the ramp; and
decoupling the drive input from a drive output of an instrument driver as the decoupling plunger cap moves.

15. The method of claim 10, wherein the slipper clutch mechanism further includes an anti-reverse mechanism that includes a spring-actuated pawl engageable with ratchet teeth defined on an inner surface of the slip carrier, the method further comprising:
allowing the slip carrier to rotate in a first direction with the pawl; and
engaging the pawl on the ratchet teeth and thereby preventing the slip carrier from rotating in a second direction opposite the first direction.

16. The method of claim 10, wherein the slipper clutch mechanism further includes a latch lock defeat mechanism that includes a column, a lifter having a foot received within a pocket defined in the column, a lifter shaft extending from the foot, and a locking tab arranged in the pocket that prevents the foot from exiting the pocket, and a ramp defined on the first ring and engageable with a lateral tab provided on the lifter shaft, and wherein rotating the first ring comprises:
moving the ramp into engagement with the lateral tab; and
moving the lifter proximally via engagement with the ramp and thereby transitioning the locking tab from a latched position, where the locking tab extends out of the pocket and inhibits unlatching of the handle from an instrument driver, and a released position, where the locking tab is stowed within the pocket and allows a latch ring to move and detach the handle from the instrument driver.

\* \* \* \* \*